United States Patent [19]

Ishido et al.

[11] Patent Number: 4,950,745
[45] Date of Patent: Aug. 21, 1990

[54] PROCESS FOR SYNTHESIS OF OLIGONUCLEOTIDES AND COMPOUND FOR FORMING POLYMERIC PROTECTING GROUP

[75] Inventors: Yoshiharu Ishido; Kazuo Kamaike, both of Tokyo, Japan

[73] Assignee: Daicel Chemical Industries, Ltd., Osaka, Japan

[21] Appl. No.: 219,156
[22] PCT Filed: Oct. 30, 1987
[86] PCT No.: PCT/JP87/00836
§ 371 Date: Jun. 27, 1988
§ 102(e) Date: Jun. 27, 1988
[87] PCT Pub. No.: WO88/03149
PCT Pub. Date: May 5, 1988

[30] Foreign Application Priority Data

Oct. 30, 1986 [JP] Japan ............... 61-256744

[51] Int. Cl.$^5$ ............... C08L 1/10; C08L 1/12; C08L 1/14; C07H 21/00
[52] U.S. Cl. ............... 536/58; 536/29; 536/55.3; 525/54.11
[58] Field of Search ............... 536/32, 23, 58, 55.3, 536/29

[56] References Cited

U.S. PATENT DOCUMENTS

| | | | |
|---|---|---|---|
| 1,924,238 | 8/1933 | Graenacher | 536/32 |
| 3,850,749 | 11/1974 | Kaufmann et al. | 195/28 N |
| 4,373,071 | 2/1983 | Itakura | 525/375 |
| 4,401,796 | 8/1983 | Itakura | 525/340 |
| 4,415,732 | 11/1983 | Caruthers et al. | 536/27 |
| 4,458,066 | 7/1984 | Caruthers et al. | 536/27 |
| 4,500,707 | 2/1985 | Caruthers et al. | 536/27 |
| 4,638,032 | 1/1987 | Benner | 525/54.11 |
| 4,667,025 | 5/1987 | Miyoshi et al. | 536/27 |
| 4,668,777 | 5/1987 | Caruthers et al. | 536/27 |
| 4,689,405 | 8/1987 | Frank et al. | 536/27 |
| 4,725,677 | 2/1988 | Koster et al. | 536/27 |
| 4,739,044 | 4/1988 | Stabinsky | 536/27 |
| 4,786,724 | 11/1988 | Letsinger | 536/27 |
| 4,812,512 | 3/1989 | Buendia et al. | 525/54.11 |
| 4,816,569 | 3/1989 | Miyoshi | 536/29 |

OTHER PUBLICATIONS

Kamaike et al., (1988) Tetrahedron Letters vol. 29, No. 2, pp. 647–650.
Cramer et al., (1966) Angew. Chem. vol. 78, 640 ff.
Hayatsu et al., (1966) J. Am. Chem. Soc., vol. 88, pp. 3182–3183.

Primary Examiner—Johnnie R. Brown
Assistant Examiner—Gary L. Kunz
Attorney, Agent, or Firm—McAulay Fisher Nissen & Goldberg

[57] ABSTRACT

A chain-extended oligonucleotide is synthesized by condensing a mononucleotide, oligonucleotide, mononucleoside succinate or oligonucleotide succinate in which only the terminal 5'-hydroxyl group is not blocked and the other functional groups are blocked by a plurality of low-molecular-weight protecting groups and one polysaccharide derivative protecting group, with a mononucleotide or oligonucleotide in which the functional groups other than the terminal phosphoric acid group ar blocked by low-molecular-weight protecting groups in the homogeneous system in a common solvent.

A compound represented by the following formula is preferred as the compound forming the polysaccharide derivative protecting group:

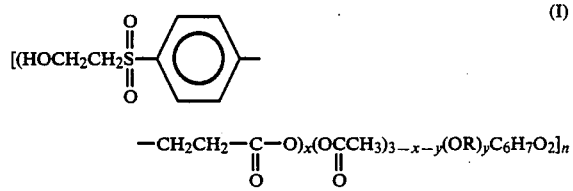

(I)

$$-CH_2CH_2-\underset{\underset{O}{\|}}{C}-O)_x(O\underset{\underset{O}{\|}}{C}CH_3)_{3-x-y}(OR)_yC_6H_7O_2]_n$$

wherein $C_6H_7O_2$ stands for an anhydrous glucose residue, R stands for

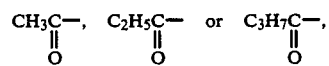

n is a number of 10 to 2,000, x is a number of 0.4 to 0.8, and y is a number of 1.0 to 2.0.

2 Claims, 2 Drawing Sheets

PROCESS FOR SYNTHESIS OF OLIGONUCLEOTIDES AND COMPOUND FOR FORMING POLYMERIC PROTECTING GROUP

TECHNICAL FIELD

The present invention relates to a process for synthesizing an oligonucleotide having a chain extended according to the bonding in nucleic acid by condensing a nucleotide or oligonucleotide. More particularly, the present invention relates to a process for synthesizing a chain-extended oligonucleotide by condensing a nucleotide or oligonucleotide having a high-molecular-weight protecting group introduced therein, in which it is possible to perform the condensation reaction in the homogeneous system and the separation and purification in the heterogeneous system and a product having a high purity can be obtained in high space-time yield.

Furthermore, the present invention relates to a compound for forming a polymeric protecting group valuable for the synthesis of the above-mentioned oligonucleotide and the synthesis of nucleic acid, oligosaccharides and polysaccharides.

BACKGROUND ART

Nucleic acid has a structure in which many hydroxyl groups at specific sites of the saccharide component of nucleotide are connected through a diester group of phosphoric acid, that is, a structure in which alcoholic hydroxyl groups of nucleotide and phosphoric acid groups are sequentially bonded through ester linkages. Accordingly, the following two methods can be adopted for condensing two nucleotides according to the bonding in nucleic acid:

(a) the method in which a 3'- or 2'-phosphoric acid group is condensed with a 5'-hydroxyl group.

(b) the method in which a 3'- or 2'-hydroxyl group is condensed with a 5'-phosphoric acid group. Since the phosphoric acid group is bulky and the 5-hydroxyl group is of a primary alcohol and has a relatively high degree of freedom, and since the 3'- and 2'-hydroxyl groups are of a secondary alcohol and close to each other, the method (a) is the most advantageous of the above-mentioned two methods. The method (a) is further divided into the diester method, the triester method, the phosphite method, and the H-phosphonate method, according to the mode of condensation reaction. In view of the reaction yield, the stability of the intermediate, the rate of reaction, and the ease of the purification of the product, the triester method and the phosphite method are considered relatively advantageous. The reaction of the triester method can be expressed by the following formula (1):

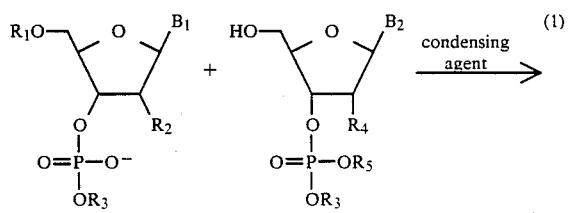

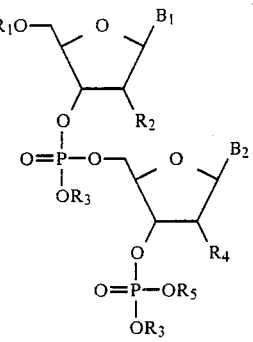

In formula (1), $B_1$ and $B_2$ stand for a base component having the amino group protected, $R_1$ stands for a protecting group for the hydroxyl group, $R_2$ and $R_4$ stand for hydrogen in the case of deoxyribonucleotide or a protected hydroxyl group in the case of ribonucleotide, and $R_3$ and $R_5$ stand for a protecting group for the phosphoric acid group.

After the above-mentioned triester-forming reaction, the protecting groups for the functional groups are removed to obtain the intended product. In general, there is no great difference in the solubility or the like of the reaction product, the unreacted substance, and the by-product, and therefore, it is not always easy separate and purify them.

Several methods have been proposed for facilitating this separation and purification by bringing about differences in the physical properties of the reaction products by using compounds having a high molecular weight as the compound forming a protecting group for the functional group. If the compound having a polymeric protecting group is solid under the reaction conditions or is obtainable as a solid after the reaction, the intended product can be easily separated and recovered by filtration and washing.

The site for forming $R_5$ in the formula (1) is considered to be the site to which the polymeric protecting group is bonded, and use of a crosslinked polystyrene or silica gel having the functional group bonded thereto as $R_5$ has been reported [V.A. Efimov et al., Nucleic Acid Res., 11, 8369 (1983)]. The oligonucleotide formed by bonding a polymeric protecting group mentioned above to the terminal phosphoric acid group is solid, and a series of solid-phase method techniques are established. In contrast, the method in which the condensation reaction represented by the formula (1) is carried out in a homogeneous solution is called the liquid phase method. In connection with the diester method, the use of polyvinyl alcohol [H. Scott et al., Makromolekular Chemie, 173, 247 (1973)], polyethylene glycol [H. Kösler, Tetrahedron Letters, No. 16, 1535 (1972)], polystyrene [H. Hayatsu, H.G. Kohorana, J. Am. Chem. Soc., 88, 3182 (1966)], and a vinyl alcohol/polyvinylpyrrolidone copolymer [H. Seliger, G. Aumamann, Tetrahedron Letters, No. 31, 2911 (1973)] as the compound for forming a polymeric protecting group has been proposed. When these solvent-soluble polymers are used, the method is regarded as a liquid-phase method, but in this case, it is not easy to separate and purify the reaction product.

DISCLOSURE OF THE INVENTION

An object of the present invention is to provide a process for synthesizing a chain-extended oligonucleotide according to the triester method or the phosphite method, in which separation and purification of the intended product can be easily carried out and the intended product having a high purity can be obtained in a high yield.

In accordance with the present invention, there is provided a process for the synthesis of a chain-extended oligonucleotide, which comprises condensing, (a) a mononucleotide, oligonucleotide, mononucleotide succinate or oligonucleotide succinate in which only the terminal 5'-hydroxyl group is not blocked and the other functional groups are blocked by a plurality of low-molecular-weight protecting groups and one polysaccharide derivative protecting group, with (b) a mononucleotide or oligonucleotide in which the functional groups other than the terminal phosphoric acid group are blocked by low-molecular-weight protecting groups in the homogeneous system in a common solvent.

Moreover, in accordance with the present invention, there is provided a compound for forming a polysaccharide derivative protecting group, which is represented by the following general formula (I):

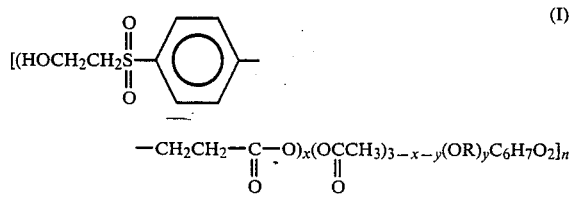

wherein $C_6H_7O_2$ stands for an anhydrous glucose residue, R stands for

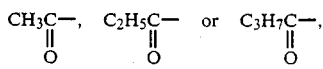

n is a number of 10 to 2,000, x is a number of 0.4 to 0.8, and y is a number of 1.0 to 2.0.

BEST MODE FOR CARRYING OUT THE INVENTION

Figure 2:
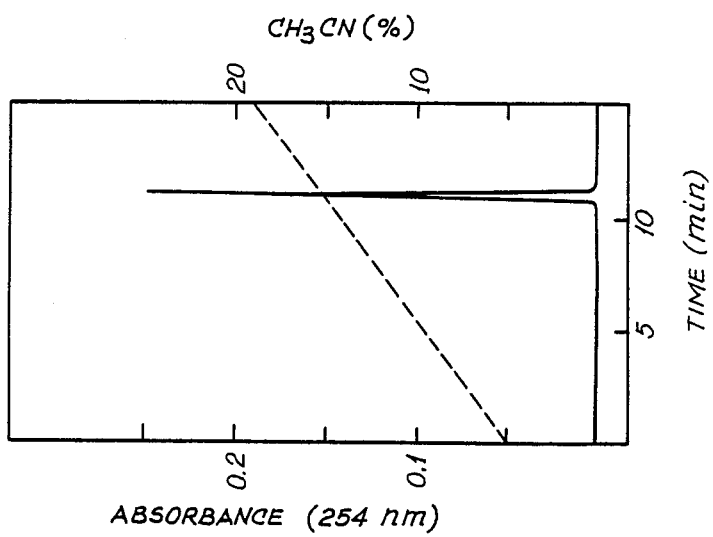
FIG. 2 is a chromatogram obtained by again subjecting a purified product of the oligonucleotide shown in FIG. 1 to chromatography.

The compound for forming a polysaccharide derivative protecting group, as used in the present invention, is soluble in a common solvent to an oligonucleotide and an oligonucleotide blocked by a low-molecular-weight protecting group, and if a non-solvent is added to a solution in this common solvent, the compound can be easily precipitated and separated. Compounds for forming a polysaccharide derivative protecting group, which are suitable for attaining the object of the present invention, can be derived from polysaccharides. Protecting group-forming compounds formed by using acetyl cellulose having a low degree of acetylation, a mixed cellulose ester composed of acetyl cellulose and propionyl cellulose or a mixed cellulose ester composed of acetyl cellulose and butyryl cellulose are especially valuable. In order to prepare a protecting group-forming compound by modifying a polysaccharide derivative, for example, acetyl cellulose, preferably a hydroxyethylsulfonyl group is introduced as the phosphoric acid group-blocking functional group. The —OH group of the hydroxyethylsulfonyl group blocks the phosphoric acid group by formation of a phosphate ester.

The skeleton of the polysaccharide derivative protecting group-forming compound constitutes a steric hindrance by reaction with a bulky compound such as nucleotide, and therefore, to impart a sufficient reactivity to the hydroxyethylsulfonyl group, the functional group must be separated from the polymeric main chain by a certain distance. Namely, the polysaccharide derivative protecting group-forming compound preferably used in the process of the present invention is an acetyl cellulose derivative in which an ester linkage is formed between the hydroxyl group of the main chain and, for example, a 4-(2-hydroxyethylsulfonyl)dihydrocinnamoyl group. Acetyl cellulose having a substitution degree of about 1.7 to about 1.8, preferred as the starting material for the protecting group-forming compound, is characterized in that the number of hydroxyl groups participating in the ester-forming reaction is large, the solubility is good, and the compound is soluble in many polar solvents.

The reaction for the synthesis of the above-mentioned acetyl cellulose derivative is illustrated by the following formulae (2) and (3).

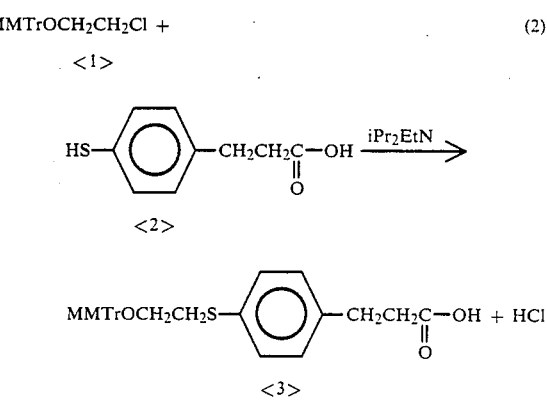

In formula (2), MMTr stands for a monomethoxytrityl group. The reaction formula (2) illustrates the synthesis of 4-(2-monomethoxytrityloxyethylthio)dihydrocinnamic acid <3> by the dehydrochlorination condensation reaction between a monomethoxytrityl ether <1> of ethylene chlorohydrin and 4-mercaptodihydrocinnamic acid <2>.

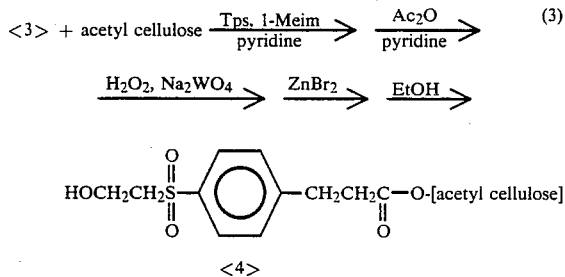

In formula (3), Tps stands for 2,4,6,-triisopropylbenzenesulfonyl chloride, and 1-Meim stands for 1-methylimidazole.

The formula (3) illustrates the reaction process in which 4-(2-monomethoxytrityloxyethylthio)dihydrocinnamic acid <3> and acetyl cellulose are subjected to ester condensation by using 1-methylimidazole as the catalyst and 2,4,6-triisopropylbenzenesulfonyl chloride as the condensing agent, unreacted hydroxyl groups in the acetyl cellulose are esterified by acetic anhydride, oxidation is effected by using hydrogen peroxide and sodium tungstate to introduce sulfonyl groups into the molecule, and a compound <4> supported by the polymer is synthesized by the removal of the monomethoxytrityl group by using zinc bromide. The compound <4> is an acetyl cellulose derivative having a 4-(2-hydroxyethylsulfonyl)dihydrocinnamoyl group. This compound is soluble in pyridine.

To simplify the explanation, the present invention will now be described with reference to the condensation reaction between a mononucleotide and a mononucleotide, but the techniques described below can be also applied to embodiments of the present invention where one or both of the reactants are oligonucleotides. In short, according to the present invention, the compound <4> is reacted with a nucleotide in which the functional groups other than one phosphoric acid group are blocked, for example, 5'-O-dimethoxytrityl-2'-O-tetrahydropyranylribonucleoside 3'-(2-chlorophenyl)-phosphate <5>, to block the phosphoric acid group, as indicated by the following formula (4):

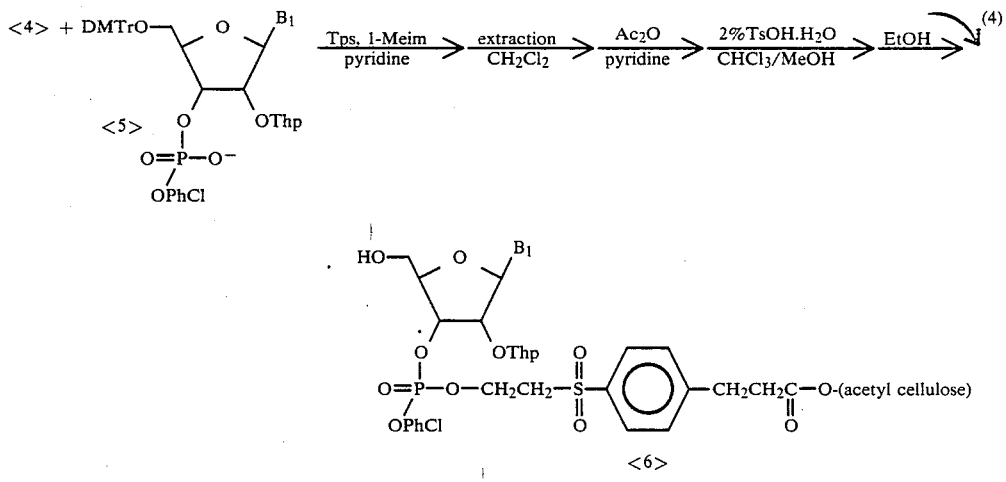

In the formula (4), DMTr stands for a dimethoxytrityl group, Thp stands for a tetrahydropyranyl group, PhCl stands for a 2-chlorophenyl group, and TsOH stands for p-toluenesulfonic acid.

Cold water is added to the liquid of the condensation reaction between <4> and <5> to stop the reaction, and if the reaction liquid is extracted with methylene chloride, the reaction product is transferred to the methylene chloride layer. The hydroxyl group of the hydroxyethyl group in <4>, which has not participated in the reaction, is blocked by an acetyl group, and p-toluenesulfonic acid is added to release the dimethoxytrityl group. If a non-solvent, that is, ethanol in this case, is added to the reaction liquid, <6> is obtained as the precipitate. The compound <6> is a mononucleotide blocked by the polysaccharide derivative protecting group.

Then, <5> and <6> are condensed to bond two nucleotides through a triester of phosphoric acid and obtain a compound <7> having the terminal phosphoric acid group blocked by the polymeric protecting group, as indicated by the following formula (5):

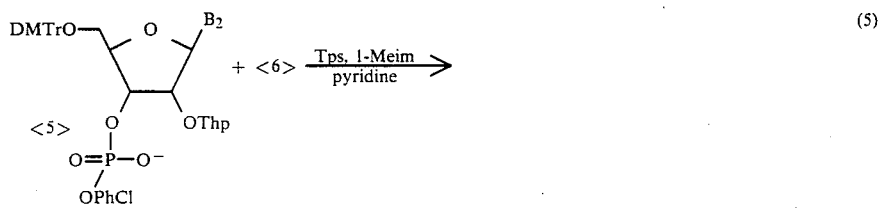

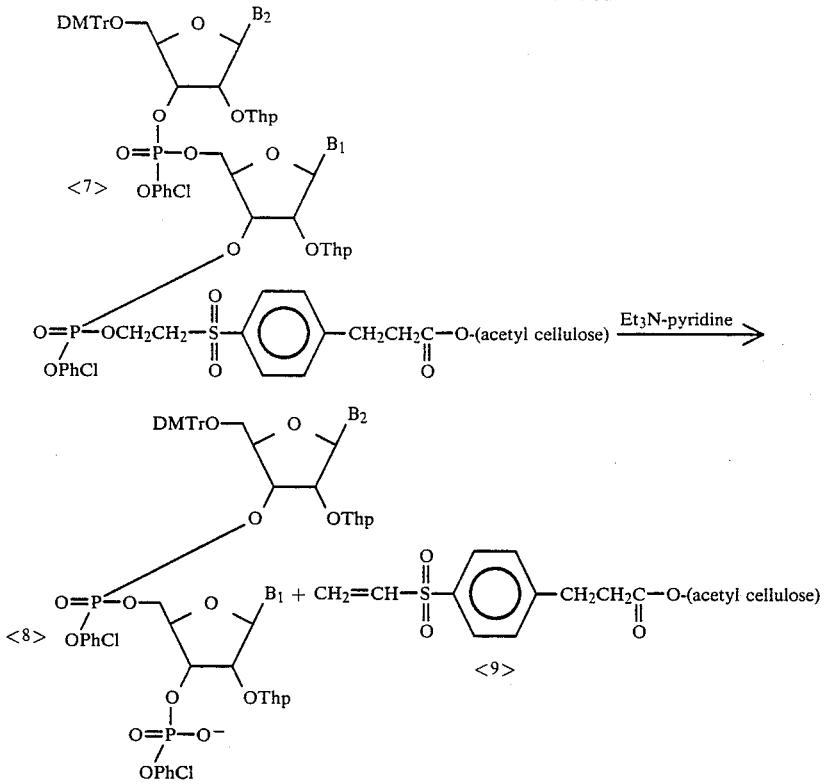

The polysaccharide derivative protecting group blocking the terminal phosphoric acid group of <7> is isolated and the product is separated, whereby the intended dinucleotide derivative <8> is obtained. This isolation reaction is a β-elimination reaction, and an acetyl cellulose derivative <9> having a terminal olefin group is formed. The derivative <9> is precipitated by adding ethanol to the reaction liquid, and can be easily separated from <8>. Separation of <8> from the unreacted nucleotide and the like is obtained by reverse phase chromatography.

The so-synthesized oligonucleotide is used in the state having the protecting group bonded thereto as the starting material for the chain-extending reaction. On the other hand, to obtain the oligonucleotide from the oligonucleotide having the protecting group bonded thereto, the protecting group is removed in the following manner. First, a treatment is carried out for 16 hours in 0.5 M 2-pyridine aldoximate - 0.5 M 1,1,3,3-tetramethylguanidine/pyridine - water (9:1 v/v) at room temperature to remove the 2-chlorophenyl group as the phosphoric acid group-protecting group, and then a treatment with aqueous ammonia (28 to 30%) is carried out at 50° C. for 5 hours to remove the protecting group for the amino group of the base portion.

Furthermore, a treatment with an aqueous hydrochloric acid solution having a pH value of 2 is carried out at room temperature for one day to remove the dimethoxytrityl group as the protecting group for the 5'-hydroxyl group and the tetrahydropyranyl group as the protecting group for the 2'-hydroxyl group.

An oligonucleotide from which the protecting groups have been completely removed is obtained according to the above-mentioned procedures.

According to the process of the present invention, optional oligonucleotides in the range of from a nucleotide dimer to a nucleotide polymer (for example, an eicosamer) can be obtained. Namely, an oligonucleotide is obtained from a mononucleotide, a high-molecular-weight oligonucleotide is obtained by condensing this oligonucleotide with a mononucleotide or oligonucleotide, and an optional polymer is obtained by repeating these procedures.

The synthesis of the chain-extended oligonucleotide has been described in detail with reference to the triester method. Nevertheless, the process of the present invention can be similarly applied to the phosphite method.

Polysaccharides, oligosaccharides and nucleic acid, which are important as physiologically active substances, are generally formed by condensing a small number of kinds of monosaccharides or mononucleotides with a certain regularity, and a pure synthesis thereof is chemically very important but involves many unsolved problems. Most of the problems encountered in the synthesis arise because it is difficult to selectively perform the reaction for leading the constituents having polyfunctional groups to a desired bonding form. Furthermore, since there is no great difference in the physical properties of the starting material, intended product, and by-product, even if the intended reaction is advanced, it is very difficult to separate and purify the intended product. For these reasons, the technique of selectively protecting each functional group of the constituents and isolating the protecting group provides an important means for synthesizing or analyzing polysaccharides, oligosaccharides, and nucleic acid.

The present invention is characterized in that the protecting group for the terminal phosphoric acid group of the nucleotide is formed of a polymeric compound which is soluble in solvents and is easily separated by precipitation, the condensation reaction is carried out in a homogeneous solution phase, and the product can be recovered by solid-liquid separation.

The characteristics of the present invention will now be described by comparing the process of the present invention with the conventional processes.

(I) Comparison with Liquid Phase Process

The main points of the conventional liquid phase process are illustrated by the following formulae (6) and (7).

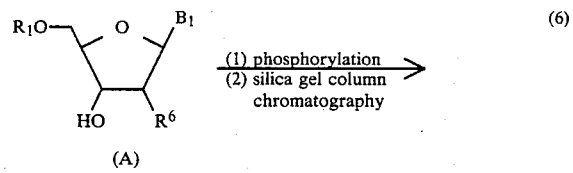

(6)

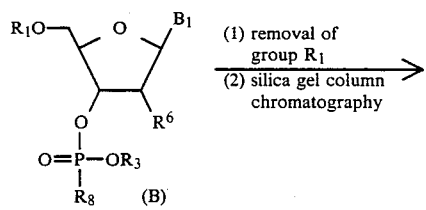

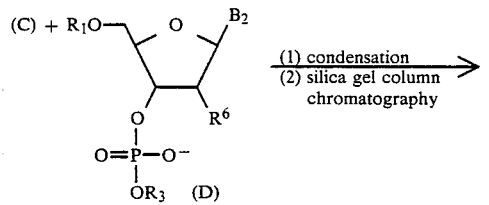

In formula (6), $R^6$ stands for —H or —$OR^7$, and $R_8$ stands for —$OR^5$ or —$NHR^9$.

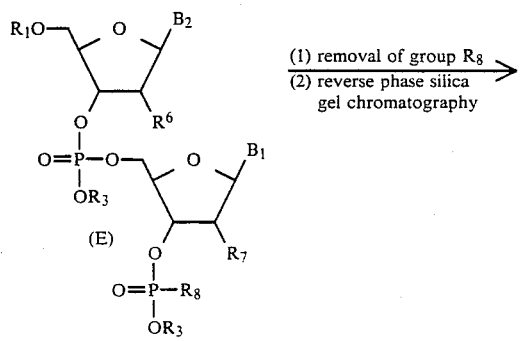

(7)

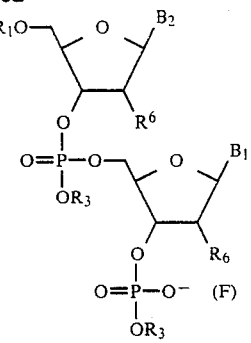

(F)

In the liquid phase process, that is, the method using only low-molecular-weight protecting groups, the products obtained at the respective steps must be able to be purified by the column chromatography. In contrast, the process of the present invention is advantageous in that the product can be easily and promptly purified by precipitating the non-solvent, and that an excessive amount of the starting material not bonded to the polymer is used and the excessive portion of the starting material is recovered at a high purity.

(II) Comparison with Solid Phase Process

In all of the conventional solid phase processes, the reaction is carried out in a heterogeneous system. Accordingly, the amount supported on the solid phase carrier, that is, the bonded amount of the starting material, is small. Even in the case of a polystyrene resin crosslinked with 1 to 2% of divinylbenzene, which is a conventional carrier considered to have a large supported amount, the amount supported of a nucleoside or nucleotide is 0.1 to 0.4 millimole/g. In contrast, in the case of acetyl cellulose used in the present invention, since the amount of the spacer introduced is 1.65 to 1.97 millimoles/g and the condensation reaction for introducing a nucleotide is advanced substantially quantitatively, a large amount of the nucleotide can be supported. Furthermore, in the conventional solid phase process, since the reaction is a heterogeneous system, it is necessary to use the condensing agent, the nucleotide or oligonucleotide 3'-phosphodiester derivative in great excess, but in the process of the present invention, since the condensation reaction is carried out in a homogeneous system, the amounts of the starting materials can be reduced and the space-time yield can be increased. In specific examples of the present invention, acetyl cellulose having a low acetylation degree (D.S.=1.7 to 1.8) is used as the starting material of the compound forming a polysaccharide derivative protecting group, and acetyl cellulose having a low acetylation degree is considered advantageous in that the acetyl cellulose has many hydroxyl groups, the acetyl cellulose is soluble in pyridine, pyridine/water and the like, hydroxyl groups not participating in the reaction can be easily blocked, and the acetyl cellulose has appropriate non-solvents.

Another characteristic feature of the compound forming a polysaccharide derivative protecting group, which is used in specific examples of the present invention, is that a spacer is introduced for bonding functional groups to the acetyl cellulose. In specific examples of the present invention, in the reaction for introducing a functional group having a spacer, 4-(2-monomethoxytrityloxyethylthio)hydroxycinnamic acid <3> is reacted. This reaction is esterification, and the amount of the reaction per unit amount of the polymer is large and the amount of the spacer introduced is large. This dominates the amount bonded of the functional group for blocking the phosphoric acid group of the nucleotide, and as a result, a large amount of the bonded nucleotide per unit amount of the polymer is obtained. In specific examples of the present invention, a 2-hydroxyethylsulfonyl group is used as the functional group for blocking the phosphoric acid group, and since the alcoholic hydroxyl group in this functional group is a primary hydroxyl group, the phosphoric acid esterification can be easily accomplished. Furthermore, since the sulfonyl group is adjacent to the carbon atom at the β-position, the functional group can be removed by β-elimination under mild conditions having no influence on other functional groups. This sulfonyl group is obtained by post-oxidizing the sulfur atom of 4-(2-monomethoxytrityloxyethylthio)dihydroxycinnamic acid <3>. This sulfur atom can be used for the determination of the introduced spacer.

The alcoholic hydroxyl group of the 2-hydroxyethylsulfonyl group of the polysaccharide derivative protecting group-forming compound used in the present invention reacts with a carboxylic acid or sulfonic acid, as well as phosphoric acid, to form an ester linkage and act as a protecting group. In the present invention, in addition to the reaction with the phosphoric acid group, a reaction is utilized in which succinic acid is bonded to the hydroxyl group of the 2-hydroxyethylsulfonyl group of the polysaccharide derivative, and the polysaccharide derivative protecting group-forming compound is used as the protecting group for the resulting carboxyl group-terminated mononucleotide succinate or oligonucleotide succinate.

EXAMPLES

The present invention will now be described in detail with reference to the following examples, that by no means limit the scope of the invention.

The synthesis of a compound forming a polysaccharide derivative protecting group is illustrated in Example 1, the synthesis of RNA type oligonucleotides is illustrated in Examples 2 through 9, and the synthesis of DNA type oligonucleotides is illustrated in Examples 10 through 15.

EXAMPLE 1

Synthesis of 4-(2-hydroxyethylsulfonyl)dihydrocinnamoylacetyl cellulose <4>

(i) 2-Chloroethyl monomethoxytrityl ether <1>

2-Chloroethanol (4.02 ml, 60 mmol) and monomethoxytrityl chloride (9.2643 g, 30 mmol) were stirred in pyridine (150 ml) at room temperature for 3 hours. Cold water (15 ml) was added to the reaction solution and the mixture was stirred for 30 minutes, and the reaction mixture was extracted with chloroform (500 ml) and washed with water (200 ml ×3 times). The organic layer was dried with anhydrous magnesium sulfate. The magnesium sulfate was removed by filtration and the filtrate was distilled under a reduced pressure. n-Hexane (100 ml) was added to the residue to effect crystallization, and thus 9.6307 g (yield=91%) of 2-chloroethyl monomethoxytrityl ether <1> was obtained.

m.p.: 87 to 88° C.

$^1$H-n.m.r. (CDCl$_3$-TMS): δ3.30–3.50 (4H, m, —C-CH$_2$×2), 3.60 (3H, s, OCH$_3$), 6.70 (2H, d, J=9 Hz, phenyl proton ×2), 6.97–7.53 (12H, m, phenyl proton ×12)

Elementary analysis values as C$_{22}$H$_{21}$O$_2$Cl:
Calculated values: C=74, 89, H=6.00
Found values: C=75.00, H=5.98

(ii) 4-Mercaptodihydrocinnamic acid <2>

4-Mercaptodihydrocinnamic acid was synthesized according to the method of Gait et al [M.J. Gait and R.C. Sheppard, Nucleic Acids Res., 4, 1135 - 1158 (1977)].

(iii) 4-(2-Hydroxyethylthio)dihydrocinnamoylacetyl cellulose <4>

2-Chloroethyl monomethoxytrityl ether <1> (2.1172 g, 6 mmol) and 4-mercaptodihydrocinnamic acid <2> (0.9112 g, 5 mmol) were dissolved in ethanol (15 ml), and diisopropylethylamine (2.45 ml, 15 mmol) was added to the solution and the mixture was heated and refluxed for 12 hours. The solvent was removed by distillation under a reduced pressure, and the residue was purified by silica gel column chromatography to obtain 1.9945 g (yield=80%) of 4-(2-monomethoxytrityloxyethylthio)dihydrocinnamic acid <3> in the form of a syrup.

$^1$H-n.m.r. (CDCl$_3$-TMS): δ2.56 (2H, t, J=7.6 Hz, C-CH$_2$), 2.83 (2H, t, J=7.6 Hz, C-CH$_2$), 3.01 (2H, t, J=6.8 Hz, C-CH$_2$), 3.32 (2H, t, J=6.8 Hz, C-CH$_2$), 3.64 (3H, s, OCH$_3$), 6.75 (2H, d, J=8.8 Hz, phenyl proton ×2), 6.98–7.45 (16H, m, phenyl proton ×16)

(iv) 4-(2-Monomethoxytrityloxyethylthio)dihydrocinnamic acid <3> (2.7924 g, 5.6 mmol) and acetyl cellulose (D.S= 1.77) (1.1794 g) were dissolved in pyridine (5 ml), and the pyridine was removed by distillation under a reduced pressure. This operation was repeated three times. Water in the mixture was removed by azeotropic dehydration and the residue was dissolved in pyridine (28 ml), 2,4,6-triisopropylbenzenesulfonyl chloride (4.0231 g, 14.0 mmol) and 1-methylimidazole (2.24 ml, 28.0 mmol) were added to the solution, and the mixture was stirred at room temperature for 2 hours.

Cold water (5 ml) was added to the reaction solution and the mixture was stirred for 30 minutes, extracted with chloroform, and washed with water. The organic layer was concentrated under a reduced pressure. The residue was subjected to azeotropic distillation with pyridine (5 ml×3 times) and dissolved in pyridine (14 ml), acetic anhydride (4.7 ml) was added to the solution, and the mixture was stirred at room temperature for 5 hours. The reaction solution was concentrated under a reduced pressure, and a small amount of toluene was added to the concentrate and azeotropic distillation was carried out under a reduced pressure until the smell of pyridine disappeared. The residue was dissolved in dioxane (130 ml) - acetic acid (9 ml) and an aqueous solution (19 ml) of Na$_2$WO$_4$.H$_2$O (0.1869 g) was added to the solution. The temperature was elevated to 80° C. and 30% aqueous hydrogen peroxide (28 ml) was dropped into the mixture over a period of 1 hour, and the mixture was stirred for 1 hour. The reaction temperature was lowered to room temperature and the reaction mixture was extracted with chloroform (150 ml) - pyridine (20 ml) and washed with water (100 ml×2 times). The organic layer was concentrated under a reduced pressure, the residue was dissolved in chloroform (30 ml), and the solution was dropped into ethanol (500 ml) with violent stirring. The formed precipitate was recovered by filtration, washed with ethanol (200 ml), and dried under a reduced pressure to obtain 2.9753 g of a white powder.

The so-obtained white powder (2.6316 g) was dissolved in a 0.7 M solution (30 ml) of zinc bromide in chloroform - methanol (7:3 v/v), and the solution was stirred at room temperature for 2 hours. The reaction solution was concentrated under a reduced pressure until the volume was reduced to about ½, and the concentrate was dropped into ethanol (400 ml) with violent stirring. The formed precipitate was recovered by filtration, washed with ethanol (100 ml), and dried under a reduced pressure to obtain 1.8160 g of 4-(2-hydroxyethylthio)dihydrocinnamoylacetyl cellulose <4> in the form of a white powder. The amount of the spacer introduced in the compound <4> was calculated as 1.65 mmol/g from the S content (5.30%, 1.65 mmol of S per gram).

EXAMPLE 2

Synthesis of dinucleotide 3'-phosohodiester derivative <8> ($B_1=B_2=N^3$-anisoyluracill-vl) by using 4-(2-hyiroxyethylsulfonyl)dihydrocinnamoylacetyl cellulose <4>

4-(2-Hydroxyethylsulfonyl)dihydrocinnamoylacetyl cellulose <4> (1.65 mmol/g) (0.2424 g, 0.4 mmol) and triethylamine $N^3$-anisoyl-5'-O-dimethoxytrityl-2'-O-tetrahydropyranyluridine 3'-(2-chlorophenyl)phosphate <5> (0.3170 g, 0.3 mmol) were dissolved in pyridine (3 ml), and the pyridine was removed by distillation under a reduced pressure. This operation was repeated three times, and water in the mixture was removed by azeotropic dehydration. The residue was dissolved in pyridine (3 ml) and 2,4,6-triisopropylbenzenesulfonyl chloride (0.2726 g, 0.9 mmol) and 1-methylimidazole (0.14 ml, 1.8 mmol) were added to the solution, and the mixture was stirred at room temperature for 1 hour. Cold water (0.5 ml) was added to the reaction solution and the mixture was stirred for 30 minutes, and methylene chloride (50 ml) was added to the mixture and the mixture was washed with water (30 ml). The organic layer was concentrated under a reduced pressure and the residue was subjected to azeotropic dehydration with pyridine (3 ml×3 times). The residue was dissolved in pyridine (7.5 ml), acetic anhydride (2.5 ml) was added to the solution, and the mixture was stirred at room temperature for 5 hours. The reaction solution was concentrated under a reduced pressure, a small amount of toluene was added to the concentrate, and azeotropic distillation under a reduced pressure was carried out until the pyridine smell disappeared.

The residue containing the acetyl cellulose derivative <4>, in which a small amount of triethylamine $N^3$-anisoyl-5'-O-dimethoxytrityl-2'-O-tetrahydropyranyluridine 3'-(2-chlorophenyl)phosphate <5> had been introduced, was dissolved in a small amount of methylene chloride, and the solution was dropped into ethanol to convert the compound <4> to a powder (3.1 mg). The dimethoxytrityl group was removed from the 5'-hydroxyl group by treatment with a 2% solution of p-toluenesulfonic acid in chloroform - methanol (7:3 v/v), and coloration was effected in 60% perchloric acid - ethanol (3:2 v/v) and the amount of the compound <5> introduced into the acetyl cellulose derivative <4> was measured by measuring the absorbance at 498 nm ($\epsilon = 72000$). It was found that the amount of the compound <5> introduced was 0.56 mmol/g, and the condensation yield was 99%.

The residue was dissolved in chloroform - methanol (7:3 v/v) (10 ml) and the solution cooled to 0° C., and a solution of p-toluenesulfonic acid monohydrate (0.3954 g) in chloroform - methanol (7:3 v/v) (5 ml) was added to the above solution. The mixture was stirred for 15 minutes, and the reaction solution was neutralized with a saturated aqueous solution of sodium hydrogencarbonate and extracted with chloroform. The organic layer was concentrated under a reduced pressure, the residue was dissolved in chloroform (10 ml), and the solution was dropped into ethanol (200 ml) with violent stirring. The formed precipitate was recovered by filtration to obtain 0.3330 g (0.224 mmol, yield=75%, 0.674 mmol/g) of the powdery compound <6> [see formula (4)].

The compound <6> (0.3330 g) and triethylamine $N^3$-anisoyl-5'-O-dimethoxytrityl-2'-O-tetrahydropyranyluridine 3'-(2-chlorophenyl)phosphate <5> (0.2958 g, 0.28 millimole) were subjected to azeotropic dehydration with pyridine (3 ml×3 times). The residue was dissolved in pyridine (2.8 ml), 2,4,6-triisopropylbenzenesulfonyl chloride (0.2544 g, 0.84 mmol) and 1-methylimidazole (0.13 ml, 0.168 mmol) were added to the solution, and the mixture was stirred at room temperature for 1 hour. Cold water (0.5 ml) was added to the reaction liquid and the mixture was stirred for 30 minutes, extracted with methylene chloride, and washed with water. The organic layer was concentrated under a reduced pressure. A small amount of the residue was dissolved in methylene chloride and the solution was dropped into ethanol to obtain a powdery product (2.9 mg). When the dimethoxytrityl group was determined, it was found that the content of the dimethoxytrityl group was 0.401 mmol/g, and the condensation yield was 97%.

The residue was dissolved in pyridine - triethylamine (3:1 v/v) (8 ml), the solution was stirred at room temperature for 2 hours, and the reaction solution was concentrated under a reduced pressure. The residue was dissolved in pyridine (10 ml) and the solution was dropped into ethanol (200 ml) with violent stirring, the formed precipitate <9> [see the formula (5)] was removed by filtration, and the filtrate was concentrated under a reduced pressure. The residue was separated by reverse phase column chromatography (eluent: 40–60% acetone 0.05 M aqueous solution of TEAB) to obtain 0.2926 g of a dinucleotide derivative <8> (0.173 mmol, 58%). At this step, 0.526 g (0.05 mmol) of the compound <5> was recovered.

The Rf value of TLC using silica gel as the carrier and the data of $^1$H-n.m.r. of the compound <8> was in agreement with that of the <8'> synthesized by the liquid phase process, and it was confirmed that <8> had the structure of <8'>. The physical property values of the compound <8> ($B_1=B_2=N^3$-anisoyluracill-yl) were as follows (the diastereomer of 2'-O-tetrahydropyranyluridine having a high polarity was used for the measurement).

$^1$H-n.m.r. (CDCl$_3$-TMS): δ1.21 (9H, t, J=7.3 Hz, CH$_2\times$3), 1.27–1.75 (12H, m C-CH$_3\times$6), 2.95 (6H, q, C-CH$_2\times$3), 3.41 —3.68 (6H, m, H-$\overline{5'}$,5' and O-CH$_2\times$2), 3.796, 3 80, 3.83 and 3.85 (12H, s×4, OCH$\overline{3}$ ×4), 4.16-5.75 (12H, m, H-5×2, 2'×2, 3' ×2, 4'×2, 5',5" and —O—C$\underline{H}$-O×2), 5.30 (1H, s, —OH), 6.05, 6.11, 6.15 and 6.27 (2H, d×4, H1'×2), 6.83–7.92 (31H, m, phenyl proton× 29 and H6×2)

Rf values: 0.28 (acetone - water, 6:4 v/v), 0.65 (acetone - water, 7:3 v/v)

EXAMPLE 3

Synthesis of dinucleotide 3'-phosphodiester derivative <8> (B$_1$ =$N$3-anisoyluracil-1-yl, B$_2$=N$^6$-benzoyladenin-9-yl) by using acetyl cellulose derivative <4>

According to the same procedures as described in Example 2, the compound <4> (1.65 mmol/g) (0.2424 g, 0.4 mmol) and triethylamine N$_3$-anisoyl-5'-O-dimethoxytrityl-2'-O-tetrahyiropyranyluridine 3'-(2-chlorophenyl) phosphate <5> (0.3170 g, 0.3 millimole) were reacted in pyridine (3 ml) as the solvent with 2,4,6-triisopropylbenzenesulfonyl chloride (0.2726 g, 0.9 mmol) and 1-methylimidazole (0.14 ml, 1.8 mmol), and the reaction mixture was treated with acetic anhydride (2.5 ml) - pyridine (7.5 ml) the condensation yield was 99%). Then, the reaction mixture was treated with a 2% solution of p-toluenesulfonic acid in chloroform - methanol (7:3 v/v), the reaction mixture was dissolved in chloroform, and the solution was dropped into ethanol to obtain 0.3680 g of the powdery compound <6> (0.255 mmol, 85%, 0.693 mmol/g).

The compound <6> (0.3680 g) and triethylamine N$^6$-benzoyl-5'-O-dimethoxytrityl-2'-O-tetrahydropyranyladenosine 3'-(2-chlorophenyl)phosphate <5> (0.3359 g, 0.32 mmol) were reacted in pyridine (3.2 ml) as the solvent with 2,4,6-triisopropylbenzenesulfonyl chloride (0.2907 g, 0.96 mmol) and 1-methylimidazole (0.15 ml, 1.92 mmol) (the condensation yield was 96%). The reaction mixture was treated with triethylamine pyridine (1:3 v/v) (8ml), and the acetyl cellulose residue was precipitated by ethanol, recovered by filtration, and separated by reverse phase silica gel column chromatography to obtain 0.2978 g of the dinucleotide derivative <8> (1.77 mmol, 59%). At this step, 0.0630 g (0.06 mmol) of the compound <5> (B$_2$=N$^6$-benzoyladenin-9-yl) was recovered. Note, the Rf value of TLC and the data of $^1$H-n.m.r. of the compound <8> was identical with that of the compound <8'> synthesized by the liquid phase process, and it was confirmed that the compound <8> had the structure of the compound <8'>.

The physical property values of the compound <8>(B$_1$=N$^3$-anisoyluracil-1-yl, B$_2$=N$^6$-benzoyladnin-9-yl) were as follows (the diastereomers of 2'-O-tetrahydropyranyluridine and 2'-O-tetrahydropyranyladenosine having a high polarity were used for the measurement).

$^1$H-n m.r. (CDCl$_3$-TMS) δ1.19–1.66 (12H, m, C—CH$_2$×6), 1.22 (9H, t, J=7.3 Hz, CH3 =3), 2.96 (6H, q, C—CH$_2$×3), 3.04–3.78 (6H, m H5', 5" and O—CH$_2$×2), 3.75 (6H, s, OCH$_3$), 3.83 (3H, s, OCH$_3$), 4.28–5.84 (11H, m, H-5, 2'×2, 3'×2, 4'×4, 5'5"and O-CH-O×2), 5.38 (1H, s, —OH), 6.15, 6.17, 6.34 and 6.39 (2H, d×4, H-1'×2), 6.76–8.67 (33H, m, phenyl proton ×30, H-2, 8 and H-6), 9.28 (1H, br–s, NH)

Rf values: 0.30 (acetone - water, 6:4 v/v), 0.67 (acetone - water, 7:3 v/v)

EXAMPLE 4

Synthesis of dinucleotide 3'-phosphodiester derivative <8> (B$_1$=B$_2$=N$^6$-benzoyladenin-9-yl by using acetyl cellulose derivative <4>

According to the same procedures as described in Example 2, the compound <4> (1.65 mmol/g) (0.6061 g, 1.00 mmol) and triethylamine N$^6$-benzoyl5'-O-dimethoxytrityl-2'-O-tetrahydropyranyladenosine 3'-(2-chlorophenyl)phosphate (0.7872 g, 0.75 mmol) were reacted in pyridine (7.5 ml) as the solvent with 2,4,6-triisopropylbenzenesulfonyl chloride (0.6814 g, 2.25 mmol) and 1-methylimidazole (0.36 ml, 4.5 mmol), and the reaction mixture was treated with acetic anhydride (6.25 ml) - pyridine (18.25 ml) (the condensation yield was 96%). The reaction mixture was treated with a 2% solution of p-toluenesulfonic acid in chloroform - methanol (7:3 v/v) and was dissolved in chloroform, and the solution was dropped into ethanol to obtain 0.9166 g of the powdery compound <6> (0.638 mmol, yield of 85%, 0.696 mmol/g). The compound <6> (0.9166 g) and triethylamine N$^6$-benzoyl 5'-O-dimethoxytrityl-2'-O-tetrahydropyranyladenosine 3'-(2-chlorophenyl)-phosphate <5> (0.8370 g, 0.80 mmol) were reacted in pyridine (8 ml) as the solvent with 2,4,6-triisopropyl-benzenesulfonyl chloride (0.7269 g, 2.40 mmol) and 1-methylimidazole (0.38 ml, 4.8 mmol) (the conversion yield was 94%). The reaction mixture was treated with triethylamine - pyridine (1:3 v/v) (20 ml), and the acetyl cellulose <9> was precipitated by ethanol, recovered by filtration and separated by reverse phase silica gel column chromatography to obtain 0.7701 g of the dinucleotide derivative <8> (0.459 mmol, yield of 61%). At this step, 0.1679 g (0.160 mmol) of the compound <5> (B$_2$=N$^6$-benzoyladenin-9-yl) was recovered.

The Rf values and the data of $^1$H-n.m.r. of the compound <8> was identical with that of the compound <8'> synthesized by the liquid phase process, and it was confirmed that the compound <8> had the structure of the compound <8'>.

The physical property values of the compound <8> (B$_1$=B$_2$=N$^6$-benzoyladenin-9-yl) were as follows (the diastereomer of 2'-O-tetrahydropyranyladenosine having a low B$_1$ polarity and a high B$_2$ polarity was used for the measurement).

$^1$H-n.m.r. (CDCl$_3$-TMS): δ1.22–1.62 (12H, m, C—CH$_2$×6), 1.25 (9H, t, J=7.3 Hz, CH3 ×3), 2.60–3.85 (6H, m, H-5', 5" and —C-CH$_2$×2), 3.00 (6H, q, —C-CH$_2$×3), 3.74 and 3.75 (6H, s×2, OCH$_3$×2), 4.53–5.51 (10H, m, H-2'×2, 3'×2, 4'×2, 5', 5" and O—CH—O×2), 5.30 (1H, s, —OH), 6.26, 6.31, 6.36 and 6.39 (2H, d×4, H-1'×2), 6.74–8.79 (35H, m, H-2×2, 8×2 and phenyl proton×31), 9.20–9.44 (2H, m, —NH ×2)

Rf values: 0.32, 0.29 (acetone - water, 6:4 v/v), 0.69, 0.66 (acetone - water, 7:3 v/v)

EXAMPLE 5

Synthesis of tetranucleotide derivative ($B_1=B_2=B_3=B_4=N^6$-benzoyladenin-9-yl) <10> having phosphodiester functional group at 3'-terminal by using 4-(2-hydroxyethylsulfonyl)dihydroxycinnamoylacetyl cellulose <4>

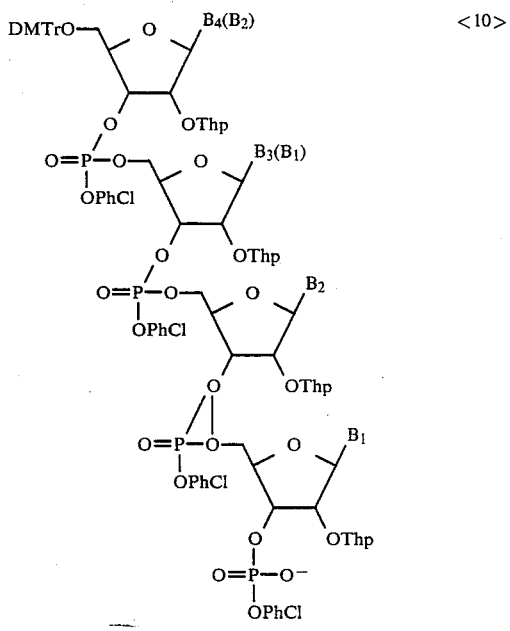

According to the same procedures as described above in synthesis (i) of <8>, the compound <4> (1.65 mmol/g) (0.3182 g, 0.525 mmol) and a compound <8> ($B_1=B_2=N^6$-benzoyladenin-9-yl) (0.5871 g, 0.35 mmol) were reacted in pyridine (10.5 ml) as the solvent with 2,4,6-triisopropylbenzenesulfonyl chloride (0.3180 g, 1.05 mmol) and 1-methylimidazole (0.17 ml, 2.10 mmol), and the reaction mixture was treated with acetic anhydride (2.5 ml) - pyridine (7.5 ml) (the condensation yield was 100%). Then, the reaction mixture was treated with a 2% solution of toluene-sulfonic acid in chloroform - methanol (7:3 v/v) and was dissolved in chloroform, and the solution was dropped in ethanol to obtain 0.6248 g of a powdery acetyl cellulose derivative having, supported thereon, a dinucleotide having a free carboxyl group at the 5'terminal (0.288 mmol, yield of 82%, 0.462 mmol/g).

This powder (0.6248 g) and a compound <8> ($B_1=B_2=N^6$-benzoyladenin-9-yl)(0.6760 g, 0.403 mmol) were reacted in pyridine (8 ml) as the solvent with 2,4,6-triisopropylbenzenesulfonyl chloride (0.3662 g, 1.21 mmol) and 1-methylimidazole (0.20 ml, 2.42 mmol) (the condensation yield was 90%).

Then, the reaction mixture was treated with triethylamine - pyridine (1:3 v/v) (10.5 ml), and the acetyl cellulose residue was precipitated by ethanol, recovered by filtration, and separated by reverse phase silica gel column chromatography to obtain 0.5095 g (0.174 mmol, yield of 50%) of a tetranucleotide derivative. At this step, 0.1778 g (0.106 mmol) of the compound <8> was recovered.

The physical property values of the compound <10> ($B_1=B_2=B_3=B_4=N^6$-benzoyladenin-9-yl) were as follows (the diastereomer of 2'-O-tetrahydropyranyladenosine having a high polarity was used for the measurement).

$^1$H-n.m.r. (CDCl$_3$–TMS): $\delta$1.12–1.76 (24H, m, C—CH$_2\times$12), 1.23 (9H, t, J=7.3 Hz, CH3 $\times$3), 2.90–3.56 (8H, m, O—CH$_2\times$4), 2.97 (6H, q, $\overline{\text{C}}$—CH$_2$-$\times$4), 3.68–3.92 (2H, m, H–5' and 5''), 3.72 (6H, s, OCH$_3\times$2), 4.12–5.72 (22H, m, H–2'$\times$4, 3'$\times$4, 4'$\times$4, 5'$\times\overline{3}$, 5''$\times$3 and O—CH—O$\times$4), 5.30 (1H, s, —OH), 6.10–6.35 (4H, m, H–1$\times$4), 6.73–8.81 (57H, m, H–2$\times$4, 8$\times$4 and phenyl proton $\times$49), 9.20–9.76 (4H, m, NH$\times$4)

Rf values: 0.10 (acetone - water, 6:4 v/v), 0.45 (acetone - water, 7:3 v/v)

EXAMPLE 6

Synthesis of 5'-O-dimethoxytrityl-O$^6$-diphenylcarbamoyl-N$^2$isobutyryl-2'-O-(tetrahydrooyran-2-yl)cuanosine 3'-succinate <11>

5'-O-Dimethoxytrityl-O$^6$-diphenylcarbamoyl-N$^2$isobutyryl-2'-O-(tetrahydropyran-2-yl)guanosine (1.6670 g, 1.78 mmol) was dissolved in methylene chloride (8.9 ml), and succinic anhydride (0.3568 g, 3.57 mmol) and DMAP (0.4362 g, 3.57 mmol) were added to the solution and the mixture was stirred at room temperature for 30 minutes. Cold water (5 ml) was added to the mixture, and the mixture was stirred at room temperature for 30 minutes and extracted with methylene chloride (50 ml). The organic layer was washed with 0.1 M TEAB (20 ml$\times$3 times) and dried with anhydrous magnesium sulfate, and magnesium sulfate was removed by filtration. The filtrate was subjected to distillation under a reduced pressure, and the residue was purified by silica gel column chromatography [2.5 cm in diameter $\times$10 cm in length, methanol - methylene chloride] to obtain 1.7370 g (the yield was 94%) of glassy 5'-O-dimethoxytrityl-O$^6$-diphenylcarbamoyl-N isobutyryl-2'-O-(tetrahydropyran-2-yl)guanosine 3'succinate <11>.

Rf value: 0.42 (CHCl$_3$–MeOH, 9:1 v/v)

$^1$H-n.m r. (CDCl$_3$–TMS): $\delta$1.12–1.19 (6H, m, C(CH$_3$)$_2$), 1.24–1.70 (6H, m, C—CH$_2$—C $\times$3), 2.51–2.84 (3H, m, C$\underline{\text{H}}$(CH$_3$)$_2$ and —CH$_2$COOH), 2.96–3.23 (2H, m, $\overline{\text{O}}$-CH2), 3.29–3.49 (2H, m, CH$_2$COO—), 3.67–3.82 (2H, m, H–5' and 5''), 3.75 , 3.74 and 3.79 (9H, s$\times$3, OCH3), 4.30–4.35 (1H, m, H–4'), 4.68–4.74 (1H, m, O—CH—O), 5.25 (1H, dd, J$_2$'$_3$'=4.88 Hz, Hz'), 5.50–5.56 (1H, m, H–3'), 6.27 (1H, d, J$_1$'$_2$'=7.81 Hz, H–1'), 6.77–7.76 (23H, m, phenyl proton$\times$23), 8.18 (1H, s, H–8), 8.31 (1H, s, N$^2$–H), 8.54–8.62 (1H, m, COO$\underline{\text{H}}$)

Elementary analysis values (C$_{57}$H$_{58}$N$_6$O$_{13}$.H$_2$O): Calculated values: C=65.01, H=5.74, N=7.98. Found values: C=64.74, H=5.62, N=7.92.

EXAMPLE 7

Synthesis of acetyl cellulose derivative <12> having supported thereon, ouanosine 3'-succinate having free 5'-hydroxyl group

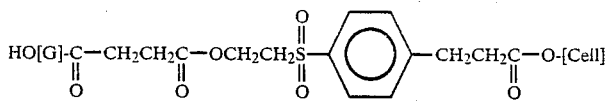

<12>

4-(2-Hydroxyethylsulfonyl)dihydrocinnamoylaOetyl cellulose <4> (1.65 mmol/g) (0.3636 g, 0.6 mmol) obtained in Example 1 and 5'-O-dimethoxytrityl-O⁶-diphenylcarbamoyl-N²-isobutyryl-2'-O-(tetrahydropyran-2yl)guanosine 3'-succinate <11> (0.4140 g, 0.4 mmol) obtained in Example 6 were subjected to axeotropic dehydration with pyridine (5 ml × 3 times), and the reaction mixture was dissolved in pyridine (6 ml). Then, 2,4,6-triisopropylbenzenesulfonyl chloride (0.3634 g, 1.2 mmol) and 1-methylimidazole (0.20 ml, 2.4 mmol) were added to the solution and the mixture was stirred at room temperature for 2 hours. Cold water (2 ml) was added to the reaction mixture, and the mixture was stirred at room temperature for 30 minutes. The reaction mixture was extracted with methylene chloride (60 ml) and washed with water (20 ml). The organic layer was concentrated and subjected to azeotropic dehydration with pyridine (5 ml × 3 times), acetic anhydride - pyridine (1:3 v/v) (15 ml) was added to the reaction mixture, and the mixture was stirred at room temperature for 5 hours. The reaction liquid was concentrated and a small amount of toluene was added, and azeotropic distillation was repeated until the pyridine smell disappeared. A small amount of the residue was dissolved in methylene chloride and the solution was dropped into ethanol with violent stirring, and the dimethoxytrityl group was determined by using a white powder (4.3 mg) obtained by refining the formed precipitate (the amount supported was 0.5 mmol/g and the condensation yield was 98%).

The remaining residue was dissolved in chloroform methanol (7:3 v/v) (5 ml), and under cooling to 0° C., a solution of p-toluenesulfonic acid monohydrate (0.3954 g) in chloroform - methanol (7:3 v/v) (5 ml) was added to the above solution and the mixture was stirred for 15 minutes, neutralized by a 5% aqueous solution of sodium hydrogencarbonate, and extracted with chloroform (100 ml). The organic layer was concentrated under a reduced pressure. The residue was dissolved in chloroform (10 ml) and the solution was dropped into ethanol (200 ml) with violent stirring. The formed precipitate was collected by filtration to obtain an acetyl cellulose derivative <12> having, supported thereon, guanosine 3'-succinate having a free 5'-hydroxyl group in a yield of 66% (0.4511 g, 0.589 mmol/g).

EXAMPLE 8

Synthesis of hexanucleotide 3'-phosphodiester derivative <13> (m=6, $B_1=B_3=B_4=L^{AN}$, $B_2=B_5=B_6=A^{BZ}$ 4-(2-Hydroxyethylsulfonyl)dihydrocinnamoylacetyl cellulose <4> (1.65 mmol/g) (0.2727 g, 0.45 mmol) obtained in Example 4 and a dinucleotide '-phosphodiester derivative <8> ($B_1=L^{AN}$, $B_2=A^{BZ}$) (0.5048 g, 0.3 mmol) were dissolved in pyridine (4.5 ml), and 2,4,6-triisopropylbenzene-sulfonyl chloride (TPS) (0.2726 g, 0.9 mmol) and 1-methylimidazole (1-Meim) (0.144 ml, 1.8 mmol) were added to the solution to effect condensation. The reaction mixture was treated with acetic anhydride (2.5 ml) - pyridine (7.5 ml) (the condensation yield was 94%). Then, the reaction mixture was treated with a 2% solution of p-toluenesulfonic acid monohydrate in chloroform - methanol (7:3 v/v) and dissolved in chloroform (10 ml). The solution was dropped into ethanol (200 ml) with violent stirring to obtain a powdery acetyl cellulose derivative having, introduced therein, a dinucleotide having a free hydroxyl group at the 5'-terminal (n=2, $B_1=U^{An}$, $B_2=A^{BZ}$)in a yield of 72% (0.5090 g, 0.427 mmol/g).

Then, the compound <14> (n=2, $B_1=U^{An}$, $B_2$ (0.5090 g) and a dinucleotide 3'-phosphodiester derivative <8> ($B_1=B_2=U^{AN}$) (0.5526 g, 0.326 mmol) were dissolved in pyridine (6.5 ml), and 2,4,6-triisopropylbenzenesulfonyl chloride (0.2962 g, 0.978 mmol) and 1-methylimidaze (0.156 ml, 1.96 mmol) were added to the solution to effect condensation (the condensation yield was 99%). The reaction mixture was dissolved in methylene chloride (10 ml) and the solution was dropped into ethanol (200 ml) with violent stirring to obtain a powdery acetyl cellulose derivative <15> having a tetramer supported thereon in a yield of 61% (0.7307 g, 0.252 mmol/g).

Note, the filtrate was concentrated and the residue was purified by reverse phase silica gel column chromatography (2.5 cm in inner diameter × 10 cm in length, 40-60% acetone - 0.05 M TEAB aqueous solution) to recover 0.1251 g (0.072 ml) of <8> ($B_1=B_2=U^{AN}$).

The powdery tetramer-supported acetyl cellulose derivative <15> (0.7306 g) obtained by repeating the above-mentioned operation was treated with acetic anhydride (2.5 ml) - pyridine (7.5 ml) and then treated with a 2% solution of p-toluenesulfonic acid monohydrate in chloroform - methanol (7:3 v/v). The reaction mixture was dissolved in chloroform (10 ml) and the solution was dropped into ethanol (200 ml) to obtain a powdery acetyl cellulose derivative <16> having, supported thereon, a tetranucleotide having a free hydroxyl group at the 5'-terminal (n=4, $B_1=B_3=B_4=U^{AN}$, $B_2=A^{BZ}$) in a yield of 47% (0.5173 g, 0.273 mmol/g).

Furthermore, <16> (n=4, $B_1=B_3=B_4=U_{AN}$, $B_2=A^{BZ}$) (0.5173 g) and <8> ($B_1=B_2=A^{BZ}$) (0.3523 g, 0.21 mmol) were dissolved in pyridine (4.2 ml), and 2,4,6-triisopropylbenzenesulfonyl chloride (0.1908 g, 0.63 mmol) and 1-methylimidazole (0.1 ml, 1.26 mmol) were added to the solution to effect condensation (the condensation yield was 84%). Then, the reaction mixture was treated with a triethylamine pyridine (1:3 v/v) solution to precipitate the residue portion of the acetyl cellulose, converted to a sulfonylalkene, from ethanol. The precipitate was recovered by filtration and separated by reverse phase silica gel column chromatography to obtain a hexanucleotide 3'-phosphodiester derivative <13> (m=6, $B_1=B_3=B_4=$, $U^{AN}$, $B_2=B_5=B_6=A^{BZ}$) in a yield of 21% (0.2527 g). At this step, 0.1310 g (0.078 mmol) of a dinucleotide 3'-phosphodiester derivative <8 22 ($B_1=B_2=A^{BZ}$) was recovered. The physical property value of the hexanucleotide 3'-phosphodiester derivative <13> (m=6, $B_1=B_3=B_4=L^{AN}$, $B_2=B_5=B_6=A^{BZ}$) were as follows.

Rf values: 0.05 (acetone - water, 6:4 v/v), 0.27 (acetone - water, 7:3 v/v)

EXAMPLE 9

(i) Synthesis of undecamer (AAAAAAUUAUG) <17> by using acetyl cellulose derivative as carrier A hexanucleotide derivative <13> (DMTr[AAU-UAU]pOH) (0.4208 g, 0.1 mmol) having a phosphodiester functional group at the 5'-terminal and the acetyl cellulose derivative <12> (0.4244 g, 0.25 mmol) having, supported thereon, guanosine 3'-succinate having a free 5'-hydroxyl group, which was obtained in Example 7, were subjected to azeotropic dehydration with pyridine (5 ml×3 times), and the reaction mixture was dissolved in pyridine (5 ml). 2,4,6-Triisopropylbenzenesulfonyl chloride (0.1211 g, 0.4 mmol) and 1-methylimidazole (0.065 ml, 0.8 mmol) were added to the solution and the mixture was stirred at room temperature for 2 hours. Then, cold water (2 ml) was added to the reaction mixture, and the mixture was stirred at room temperature for 30 minutes, extracted with methylene chloride (60 ml), and washed with water (20 ml). The organic layer was concentrated and subjected to azeotropic dehydration with pyridine (5 ml×3 times), acetic anhydride - pyridine (1:3 v/v) (10 ml) was added to the residue, and the mixture was stirred at room temperature for 5 hours. The reaction solution was concentrated, and a small amount of toluene was added to the residue and azeotropic distillation was repeated until the pyridine smell disappeared (the concentration yield was 98%, 0.117 mmol/g). The residue was dissolved in chloroform - methanol (7:3 v/v) (10 ml), and under cooling to 0° C., a solution of p-toluenesulfonic acid monohydrate (0.3954 g) in chloroform - methanol (7:3 v/v) (10 ml) was added to the solution. The mixture was stirred for 15 minutes, neutralized with a 5% aqueous solution of sodium hydrogencarbonate and extracted with chloroform (100 ml), and the organic layer was concentrated under a reduced pressure. The residue was dissolved in chloroform (10 ml) and the solution was dropped into ethanol (200 ml) with violent stirring. The formed precipitate was collected by filtration to obtain an acetyl cellulose derivative <18> having, supported thereon, a heptamer having a hydroxyl group at the 5'-terminal in a yield of 87% (0.7210 g, 0.121 mmol/g).

The so-obtained cellulose derivative <18> (0.7210 g, 0.087 mmol) and the tetranucleotide derivative <10> having a phosphodiester functional group at the 3'-terminal (DMTr[AAAA]pOH) (0.6424 g, 0.219 mmol), which was obtained in Example 5, were subjected to azeotropic dehydration with pyridine (5 ml×3 times), and the residue was dissolved in pyridine (8.7 ml). 2,4,6-Triisopropylbenzenesulfonyl chloride (0.1990 g, 0.657 mmol) and 1-methylimidazole (0.107 ml, 1.314 mmol) were added to the solution, and the mixture was stirred at room temperature for 2 hours. Then, cold water (2 ml) was added to the reaction mixture, and the mixture was stirred at room temperature for 30 minutes, extracted with methylene chloride (100 ml), and washed with water (30 ml). The organic layer was concentrated under a reduced pressure, the residue was dissolved in methylene chloride (10 ml), and the solution was dropped into ethanol (200 ml) with violent stirring. The formed precipitate was collected by filtration to obtain an acetyl cellulose derivative <19> having an undecamer supported thereon in an overall yield of 69% (0.7911 g, 0.087 mmol/g) (the condensation yield was 96%). Note, 0.2180 g (0.074 mmol) of the tetranucleotide derivative <10> was recovered from the filtrate by removing ethanol by distillation and performing purification by reverse phase silica gel column chromatography.

(ii) Removal of protecting group from undecamer (AAAAAAUUAUG)

The undecamer-supported acetyl cellulose derivative <19> (44.8 mg, 3.97 mmol) was dissolved in a 0.5 M solution of 2-pyridinecarboxyaldoxime-1,1,3,3-tetramethylguanidine in pyridine - water (9:1 v/v) (0.6 ml), and the solution was allowed to stand at room temperature for 1 day. Ethanol (30 ml) was added to the reaction solution to precipitate the acetyl cellulose derivative residue <9>, from which the undecamer had been set free, and centrifugal separation was carried out (3000 rpm, 4° C., 10 minutes) and the supernatant was concentrated. Concentrated aqueous ammonia (28%) (20 ml) was added to the residue, and the mixture was sealed, allowed to stand at 55° C. for 6 hours and concentrated under reduced pressure. SEP-PAK (C-18) (Waters Co.), which had been allowed to stand for more than 3 hours after injection of acetonitrile - water (9:1 v/v) (10 ml), was washed with 20 ml of 50 mM TEAB (prepared by diluting 1 M TEAB having a pH value of 8.0), and the sample (residue) dissolved in 50 mM TEAB (20 ml) was injected into the washed SEP-PAK (C-18) (Waters Co.)

Figure 1:
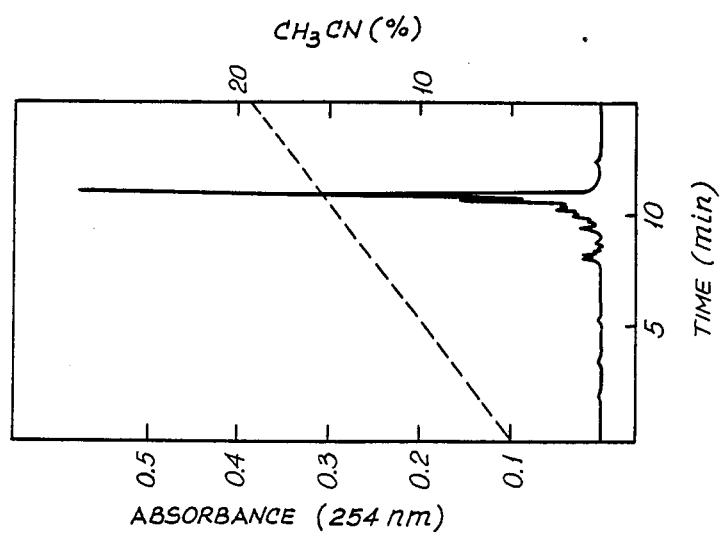
FIG. 1 is a chromatogram obtained by a reverse phase high-performance liquid chromatography of an oligonucleotide (RNA type undecamer) from which the protecting groups have been completely removed, obtained in an example (Example 9) of the present invention.

2-Pyridinecarboxyaldoxime and 1,1,3,3-tetramethylguanidine were eluted out by 15% acetonitrile - 50 mM TEAB (30 ml) and then by 18% acetonitrile - 50 mM TEAB (10 ml), and the undecamer was eluted out by 35% acetonitrile - 50 mM TEAB (10 ml) and the eluate was freeze-dried. The residue was dissolved in water (1 ml) and the sample (0.1 ml) was purified by HPLC (M & S PACK C-18, 4.6 mm in inner diameter×150 mm in length, 10–50% acetonitrile - 0.1 M TEAA). (The obtained results are shown in FIG. 1.) The eluate was confirmed by a UV monitor (280 nm), and the central portion of the main peak was collected and concentrated under reduced pressure. Water (1 ml) was added to the concentrate and distillation under a reduced pressure was conducted until the triethylamine disappeared. The residue was dissolved in an aqueous hydrochloric acid solution (5 ml) having a pH value of 2.0 and the solution was allowed to stand at room temperature for 2 days. The solution was neutralized with dilute aqueous ammonia and washed with ethyl acetate (10 ml×3 times), and the aqueous phase was concentrated under a reduced pressure. The sample (residue) was dissolved in water (200 μl) and the sample (180 μl) was purified by HPLC (M & S PACK C-18, 4.6 mm in inner diameter×150 mm in length, 5–19% acetonitrile - 0.1 M TEAA). (The obtained results are shown in FIG. 2.) At this step, the eluate was confirmed by a UV monitor, and the central portion of each peak was collected and freeze-dried to obtain 1.51 OD of an undecamer (ApApApApApApUpUpApUpG), from which all the protecting groups had been removed.

(iii) Confirmation of structure of undecamer (ApApApApApApUpUpApUpG)

1 M Ammonium acetate buffer (pH 5.3) (10 μl) and Nuclease P1 (Yamasa Shoyu Co., 1 mg/5μl) (3 μl) were added to an aqueous solution (86.32 μl) of the protecting group-removed undecamer <17> (0.1 OD), and the mixture was allowed to stand at 37° C. for 30 minutes.

The enzyme decomposition product was separated by HPLC (M & S PACK C-18, 4.6 mm in inner diameter × 150 mm in length).

The undecamer was completed decomposed to obtain a decomposition product comprising adenosine, guanosine 5-phosphate, uridine 5'-phosphate and adenosine 5'-phosphate at a ratio of 1.38:1.31:3.00:5.95.

It is said that Nuclease P1 has a property of further decomposing adenosine 5'-phosphate to adenosine. The ratio determined in consideration of this fact, that is, the ratio of (adenosine + adenosine 5'-phosphate): uridine 5'-phosphate:guanosine 5'-phosphate, is 7.00:2.87:1.25.

EXAMPLE 10

Synthesis of di-2'-deoxyribonucleotide 3'-phosphodiester derivative <20> ($B_1=B_2=T^{BZ}$) supported on acetyl cellulose derivative <4>

A di-2'-deoxyribonucleotide 3'-phosphodiester <20> ($B_1=B_2=T^{BZ}$) was synthesized from 4-(2-hydroxyethylsulfonyl)dihydrocinnamoylacetyl cellulose <4> obtained in Example 1 according to the following reaction formula:

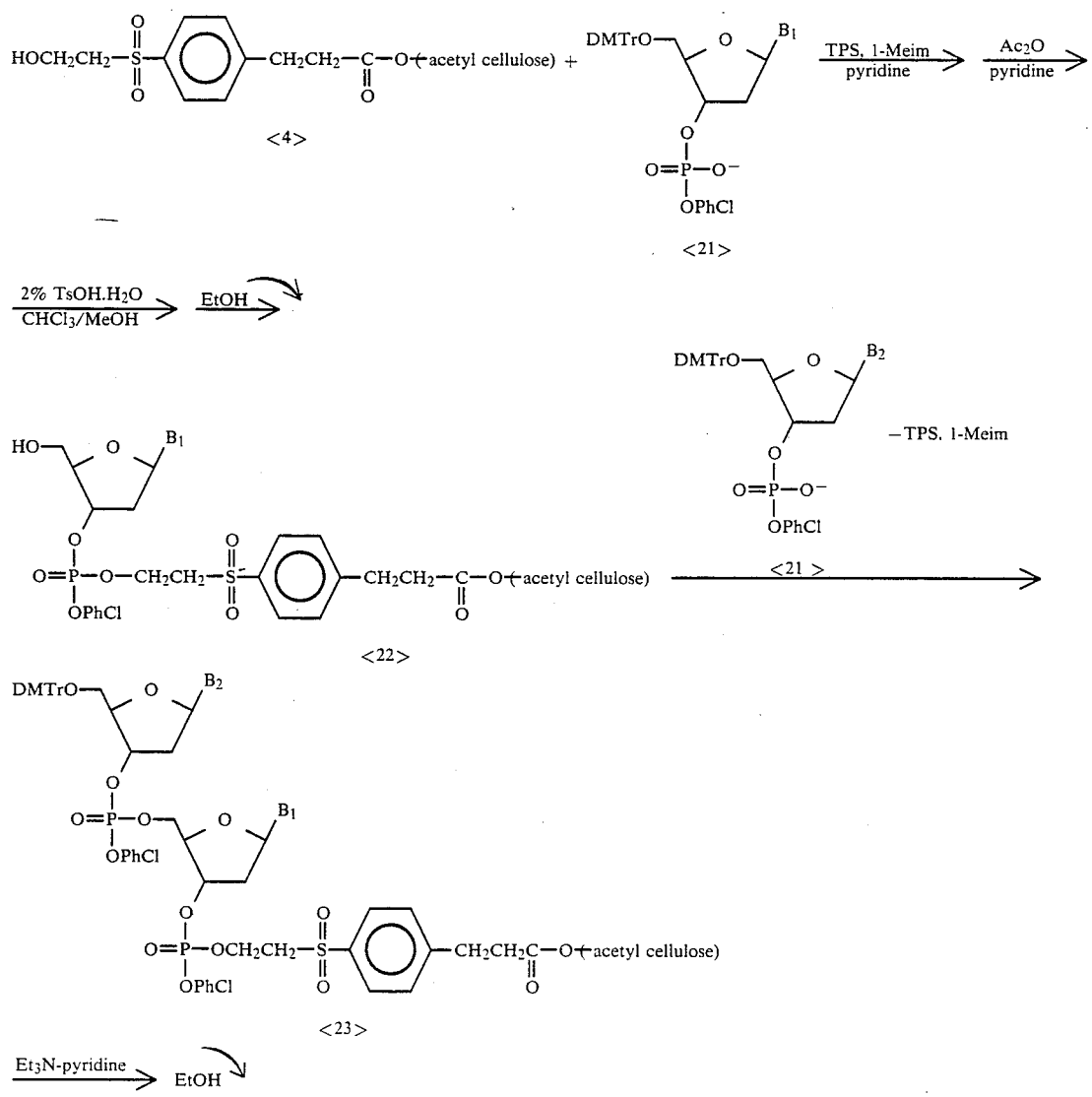

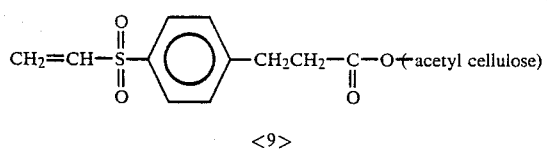

<9>

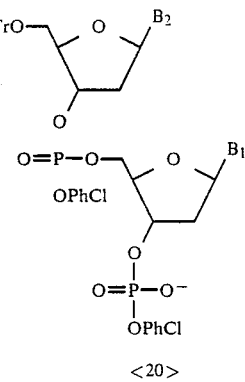

<20>

The acetyl cellulose derivative <4> (1.65 mmol/g) (0.3272 g, 0.53 mmol) obtained in Example 1 and triethylammonium $N^3$-benzoyl-5'-O-dimethoxytritylthymidine 3'-(2-chlorophenyl)phosphate <21> (0.3766 g, 0.4 mmol) were dissolved in pyridine (3 ml), and the pyridine was removed by distillation under a reduced pressure. This operation was repeated 3 times to remove water in the mixture by azeotropic distillation. The residue was dissolved in pyridine (4 ml) and 2,4,6-triisopropylbenzenesulfonyl chloride (0.3634 g, 1.2 mmol) and 1-methylimidazole (0.19 ml, 2.4 mmol) were added to the solution, and the mixture was stirred at room temperature for 1 hour. Cold water (0.5 ml) was added to the reaction solution and the mixture was stirred for 30 minutes, and the reaction solution was concentrated under a reduced pressure. Pyridine (3 ml×3 times) was added, and removed by distillation under a reduced pressure to remove water in the mixture by azeotropic dehydration. The residue was dissolved in pyridine (9 ml) and acetic anhydride (3 ml) was added to the solution, and the mixture was stirred at room temperature for 5 hours. The reaction solution was concentrated under a reduced pressure. A small amount of toluene was added to the residue, and distillation under a reduced pressure was conducted until the pyridine smell disappeared. A very small amount of the acetyl cellulose derivative having <21> introduced therein was dissolved in a small amount of methylene chloride and the solution was dropped into ethanol, and the formed precipitate was collected by filtration and dried under a reduced pressure to obtain a powder (4.6 mg).

A 2% solution (1 ml) of p-toluenesulfonic acid in chloroform - methanol (7:3 v/v) was added to the powder and the mixture was allowed to stand at room temperature for 15 minutes to remove the dimethoxytrityl group, and coloration was effected by 60% perchloric acid methanol (3:2 v/v). By measuring the absorbance at 498 nm ($\epsilon$=72000), the amount of <21> introduced in the acetyl cellulose derivative was determined. It was found that the amount introduced of <21> was 0.604 mmol/g, and the condensation yield was 100%.

The remaining acetyl cellulose derivative having methanol (7:3 v/v) (8 ml), and under cooling to 0° C., a solution (4 ml) of p-toluenesulfonic acid monohydrate (0.3164 g) in chloroform - methanol (7:3 v/v) was added to the above solution and the mixture was stirred for 15 minutes. Then, pyridine (1 ml) was added to the mixture and the reaction solution was concentrated under a reduced pressure until the volume was reduced to about ½. The residual solution was dropped into ethanol (200 ml) with violent stirring, and the formed precipitate was recovered by filtration and dried under a reduced pressure to obtain a powdery acetyl cellulose derivative <22> ($B_1 = T^{Bz}$) having, supported thereon, a thymidine 3'-phosphate derivative having a free hydroxyl group at the 5'-position in a yield of 95% (0.5120 g, 0.378 mmol; 0.739 mmol/g). <22> ($B_1 = T^{Bz}$) and <21> ($B_2 = T^{Bz}$) (0.449 g, 0.473 mmol) were added to pyridine (3 ml×3 times) and water in the mixture was removed by azeotropic dehydration. The mixture was dissolved in pyridine (9.5 ml) and 2,4,6-triisopropylbenzenesulfonyl chloride (0.4298 g, 1.42 mmol) and 1-methylimidazole (0.225 ml, 2.84 mmol) were added to the solution, and the mixture was stirred at room temperature for 1 hour (0.432 mmol/g, condensation yield =99%). Cold water (1 ml) was added to the reaction solution, the mixture was stirred at room temperature for 30 minutes, and the reaction solution was concentrated under a reduced pressure.

Then, the residue was dissolved in triethylamine pyridine (1:3 v/v) (16 ml) and the solution was stirred at room temperature for 2 hours. The residual portion <9> of the acetyl cellulose derivative converted to the sulfonylalkene was precipitated from ethanol (100 ml) and removed by filtration. The filtrate was concentrated under a reduced pressure and separated by reverse phase silica gel chromatography (10 to 40% acetone–0.05 M TEAB system) to obtain <20> (B<<22>>(Bl =$T_1 = B_2 = T^{Bz}$) in a yield of 63% (0.3710 g, 0.254 mmol). At this step, 0.789 g (0.083 mmol) of <21> (B=$T^{Bz}$) was recovered.

The physical properties of <20> ($B_1 = B_2 = T^{Bz}$) are as follows.

Rf value: 0.29 (acetone - water, 6:4 v/v) $^1$H-n.m.r. (CDCl$_3$- TMS): δ1.24 (9H, t, J=7.3 Hz, [C—CH$_3$ in N—C$_2$H$_5$ group]×3), 1.27 (3H, s, CH$_3$-5), 1.35 (3H, s CH$_3$-5), 2.05–2.70 (4H, m, H-2'×2 and H-2"33 2), 2.97 (6H, q, C—CH$_2$-N×3), 3.78 (6H, s, OCH$_3$×2), 3.30–4.50 (6H, m, H-4'×2, H-5'×2 and H-5"×2), 4.95–5.40 (2H, m, H-3'×2), 6.29–6.45 (2H, m, H-1'×2) and 6.30–8.60 (33H, m, phenyl proton×31 and H-6 ×2)

EXAMPLE 11

Synthesis of di-2'-deoxyribonucleotide 3'-phosphodiester derivative <20> ($B_1 = B_2 = A^{Aca}$) by using acetyl cellulose derivative <4> as carrier According to the reaction formula described in Example 10, a di-2'-deoxyribonucleotide-3-phosphodiester derivative <20> ($B_1 = B_2 = A^{Aca}$) was synthesized from the acetyl cellulose derivative <4>.

More specifically, in the same manner as described in Example 10, <4>(1.65 mmol/g) (0.3272 g, 0.53 mmol) and triethylammonium 5'-O-dimethoxytritylN$^6$-(dimethylamino)ethylene-2'-deoxyadenosine 3'-(2-chlorophenyl)phosphate <21> (0.3882 g, 0.4 mmol) were dissolved in pyridine (4 ml), and 2,4,6-triisopropylbenzenesulfonyl chloride (0.3634 g, 1.2 mmol) and 1-methylimidazole (0.19 ml, 2.4 mmol) were added to the solution and the mixture was stirred at room temperature for 1 hour. Cold water (1 ml) was added to stop the reaction, and the reaction solution was concentrated under a reduced pressure and treated with acetic anhydride - pyridine (1:3 v/v) (12 ml) (0.590 mmol/g, condensation yield=99%). Then, the reaction solution was treated with a solution (12 ml) of p-toluenesulfonic acid monohydrate (0.3164 g) in chloroform - methanol (7:3 v/v) and dropped into ethanol (200 ml) with violent stirring to obtain powdery <22> ($B_1 = A^{Aca}$) in a yield of 89% (0.4970 g, 0.357 mmol; 0.717 mmol/g).

<22> ($B_1 = A^{Aca}$) and <21> ($B_2 = A^{Aca}$) (0.4325 g, 0.446 mmol) were dissolved in pyridine (9 ml), and 2,4,6-triisopropylbenzenesulfonyl chloride (0.3377 g, 1.34 mmol) and 1-methylimidazole (0.21 ml, 2.68 mmol) were added to the solution and the mixture was stirred at room temperature for 1 hour. Cold water (1 ml) was added to stop the reaction and the reaction solution was concentrated under a reduced pressure so that the volume was reduced to about ½, and the concentrate was dropped into ethanol (200 ml) with violent stirring to obtain a powdery dinucleotidesupported acetyl cellulose derivative <23> in a yield of 0.6900 g, 0.283 mmol (0.410 mmol/g, condensation yield =97%).

The acetyl cellulose derivative residue <9> converted to a sulfonylalkene by the treatment with triethylamine - pyridine (1:3 v/v) (16 ml) was precipitated from ethanol (100 ml), recovered by filtration, and separated by reverse phase silica gel chromatography to obtain <20> ($B_1 = B_2 = A^{Aca}$) in a yield of 63% (0.3710 g, 0.254 mmol). At this step, 0.0789 g (0.083 mmol) of <21> ($B = A^{Aca}$) was recovered.

The physical properties of <20> ($B_1 = B_2 = A^{Aca}$) are as follows.

Rf value: 0.34 (acetone - water, 6:4 v/v) $^1$H-n.m.r. (CDCl$_3$- TMS) δ1.27 (9H, t, J=7.3 Hz, [C—CH$_3$in N-ethyl group]×3), 2.10 (6H, s, C(CH$_3$) of N(CH$_3$)$_2$×2), 2.85-2.90 (4H, m, H-2'×2 and H-2"×2), 2.90 (6H, q, C—CH$_2$-N×3), 3.13 (12H, m, N(CH$_3$)$_2$×2), 3.34 (4H, m, H-5'×2 and H-5"×2), 3.72 (6H, s, O-CH$_3$×2), 4.40 (2H, m, H-4'×2), 5.40-5.55 (2H, m, H-3'×2), 6.36-6.50 (2H, m, H-1'×2), 6.70-7.50 (21H, m, phenyl proton×21), 8.00 (2H, s, H-2×2) and 8.55 (2H, s, H-8×2)

EXAMPLE 12

Synthesis of di-2'-deoxyribonucleotide 3'-phosphodiester derivative <20> ($B_1 = B_2 = G^{Dpc,iBu}$) by using acetyl cellulose derivative <4> as carrier According to the reaction formula described in Example 10, a di-2'-deoxyribonucleotide 3'-phosphodiester derivative <20> ($B_1 = B_2 = G^{Dpc,iBu}$) was synthesized from the acetyl cellulose <4>.

More specifically, in the same manner as described in Example 10, <4> (1.65 mmol/g) (0.2424 g, 0.4 mmol) and triethylammonium 5'-O-dimethoxytritylN$^6$-diphenylcarbamoyl-N$^2$-isobutyryl-2-deoxyguanosine-3'(2-chlorophenyl)phosphate <21> ($B_1 = G^{Dpc,iBu}$) (0.3375 g, 0.3 mmol) were dissolved in pyridine (3 ml), and 2,4,6-triisopropylbenzenesulfonyl chloride (0.2726 g, 0.9 mmol) and 1-methylimidazole (0.144 ml, 1.8 mmol) were added to the solution and the mixture was stirred at room temperature for 1 hour. Cold water (1 ml) was added to stop the reaction, and the reaction solution was concentrated under a reduced pressure and treated with acetic anhydride - pyridine (1:3 v/v) (10 ml) (0.533 mmol/g, condensation yield=98%). Then, the reaction solution was treated with p-toluenesulfonic acid monohydrate (0.3164 g) and chloroform - methanol (7:3 v/v) (12 ml) and dropped into ethanol (200 ml) with violent stirring to obtain powder <22> ($B_1 = G^{Dpc,iBu}$) in a yield of 88% (0.4150 g, 0.264 mmol; 0.635 mmol/g). <22> ($B_1 = G^{Dpc,iBu}$) and <21> ($B_2 = G^{Dpc,iBu}$) (3708 , 0.33 mmol) were dissolved in pyridine (6.6 ml), and 2,4,6-triisopropylbenzenesulfonyl chloride (0.2999 g, 0.99 mmol) and 1-methylimidazole (0.16 ml, 1.98 mmol) were added to the solution and the mixture was stirred at room temperature for 1 hour. Cold water (1 ml) was added to stop the reaction and the reaction solution was concentrated under a reduced pressure (0.356 mmol/g, condensation yield=95%). The concentrate was treated with triethylamine - pyridine (1:3 v/v) (8 ml) and the acetyl cellulose derivative residue <9> converted to a sulfonylalkene was precipitated from ethanol (100 ml), recovered by filtration, and separated by reverse phase silica gel column chromatography to obtain <20> ($B_1 = B_2 = G^{Dpc,iBu}$) in a yield of 51% (0.2797 g, 0.153 mmol). At this step, <21> ($B = G^{Dpc,iBu}$) was recovered in an amount of 0.0496 g (0.0441 mmol).

The physical properties of <20> ($B_1 = B_2 = G^{Dpc,iBu}$) are as follows.

Rf value: 0.17 (acetone - water, 6:4 v/v) $^1$H-n.m.r. (CDCl$_3$- TMS): δ1.05-1.25 (21H, m [C-CH$_3$in N-ethyl group]×3 and CH(CH$_3$)$_2$×2), 2.50-3.45 (14H, m, C—CH$_2$-N×3, CH(CH$_3$)$_2$×2, H-2'×2, H -2"×2, H-5'×2 and H-5"×2), 3.70 (6H, s, OCH$_3$×2), 4.50-4.65 (2H, m, H-4'×2), 5.30-5.55 (2H, m, H-3'×2), 6.30 -6.45 (2H, m, H-1'×2), 6.66-7.64 (41H, m, phenyl proton×41), 8.05 and 8.07 (2H, s×2, H-8×2) and 8.55 and 8.80 (2H, s×2, NHCO×2)

EXAMPLE 13

Synthesis of tri-2'-deoxyribonucleotide-3'-phosphodiester derivative <24> ($B_1 = C^{AN}$, $B_2 = B_3 = T^{BZ}$) by using acetyl cellulose derivative <4> as the carrier A tri-2'-deoxyribonucleotide 3'-phosphodiester derivative <24> was synthesized from the acetyl cellulose derivative <4> according to the following reaction formula:

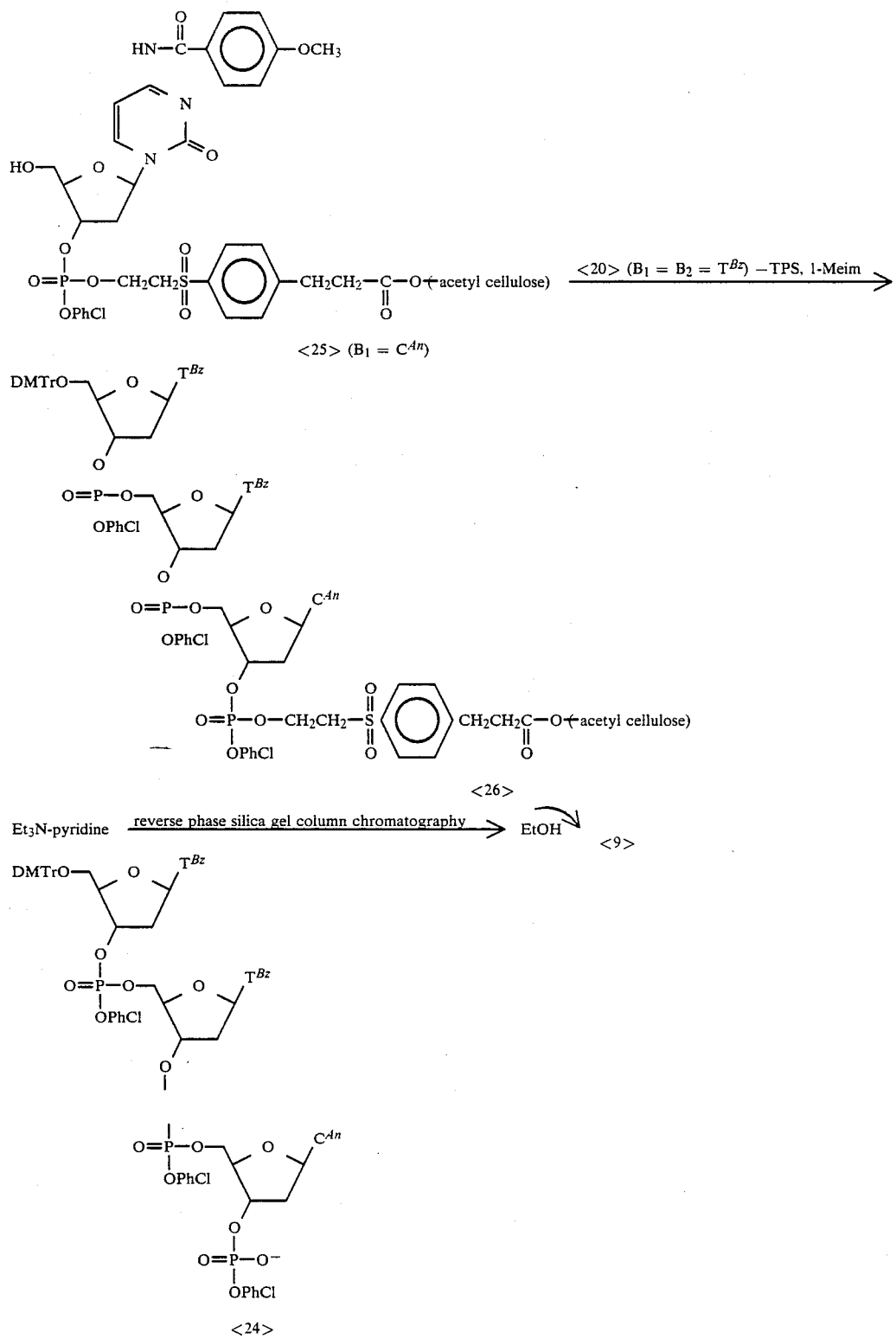

The acetyl cellulose derivative <4> (1.63 mmol/g) (0.8650 g, 1.39 mmol) obtained in Example 1 and $N^4$-anisoyl-5'-O-dimethoxytrityl-2'-deoxycytidine 3'-(2-chlorophenyl)phosphate <21> (0.9550 g, 1 mmol) were subjected to azeotropic dehydration with pyridine (5 ml×3) to remove water from the system, and the mixture was dissolved in pyridine (10 ml). Then, 2,4,6-triisopropylbenzene-sulfonyl chloride (0.9086 g, 3 mmol) and 1-methylimidazole (0.48 ml, 6 mmol) were added the solution and the mixture was stirred at room temperature for 4 hours. Cold water (0.5 ml) was added to the reaction solution to stop the reaction, and the reaction mixture was concentrated under a reduced pressure, water was removed from the reaction mixture by axeotropic dehydration with pyridine (5 ml×3 times), the residue was dissolved in pyridine (7.5 ml), acetic anhydride (2.5 ml) was added to the solution and the mixture was stirred at room temperature for 5 hours. The reaction solution was concentrated under a reduced pressure, and a small amount of toluene was added to the concentrate and distillation under a reduced pressure was conducted until the pyridine smell was not felt (0.554 mmol/g, condensation yield=82%).

Then, the residue was dissolved in a solution (20 ml) of p-toluenesulfonic acid monohydrate (0.5412 g) in chloroform - methanol (7:3 v/v), and the solution was stirred at 0° C. for 15 minutes, neutralized with pyridine, and concentrated under a reduced pressure. The residue was dissolved in methylene chloride (10 ml) and the solution was dropped into ethanol (100 ml) with violent stirring. The formed precipitate was recovered by filtration and dried under a reduced pressure to obtain powdery <25> ($B_1=C^{An}$) in a yield of 64%

Then, <25>p0 ($B_1=C^{AN}$) and <20> ($B_1=B_2=$(0.7565 g, 0.518 mmol) were subjected to azeotropic dehydration with pyridine (5 ml×3 times) to remove water in the system, and the mixture was dissolved in pyridine (10 ml) and 2,4,6-triisopropylbenzenesulfonyl chloride (0.4840 g, 1.60 mmol) and 1-methylimidazole (0.26 ml, 3.2 mmol) were added to the solution. The mixture was stirred at room temperature for 4 hours. Cold water (0.5 ml) was added to the reaction solution, and the mixture was stirred at room temperature for 30 minutes and concentrated under a reduced pressure to obtain <26>.

The residue was dissolved in triethylamine pyridine (1:3 v/v) (20 ml), and the solution was stirred at room temperature for 2 hours and concentrated under a reduced pressure. The residue as dissolved in methylene chloride (10 ml) and the solution was dropped into ethanol (100 ml) with violent stirring to precipitate the acetyl cellulose derivative residue <9> converted to a sulfonylalkene. The precipitate was removed by filtration, and the filtrate was concentrated under a reduced pressure and separated by the reverse phase silica gel column chromatography (10 to 40% acetone M TEAB system) to obtain <24> ($B_1=C^{An}$, $B_2$ and $B_3=T^{BZ}$) in a yield of 47% (0.5180 g, 0.25 mmol).

The physical property values of <24> ($B_1=C^{An}$, $B_2=B_3=T^{BZ}$) are as follows.

Rf values: 0.19 (acetone - water, 6:4 v/v), 0.43 (acetone - water, 7:3 v/v)

EXAMPLE 14

Synthesis tetra-2'-deoxyribonucleotide 3'-phosphodiester derivative <27> ($B_1=B_2=A^{Aca}$, $B_3=B_4=G^{Dpc,iBu}$) by using acetyl cellulose derivative <4> as the carrier A tetra-2'-deoxyribonucleotide 3'-phosphodiester derivative <27> ($B_1=B_2=A^{Aca}$, $B_3=B_4=G^{Dpc,iBu}$) was synthesized from the acetyl cellulose derivative according to the following reaction formula:

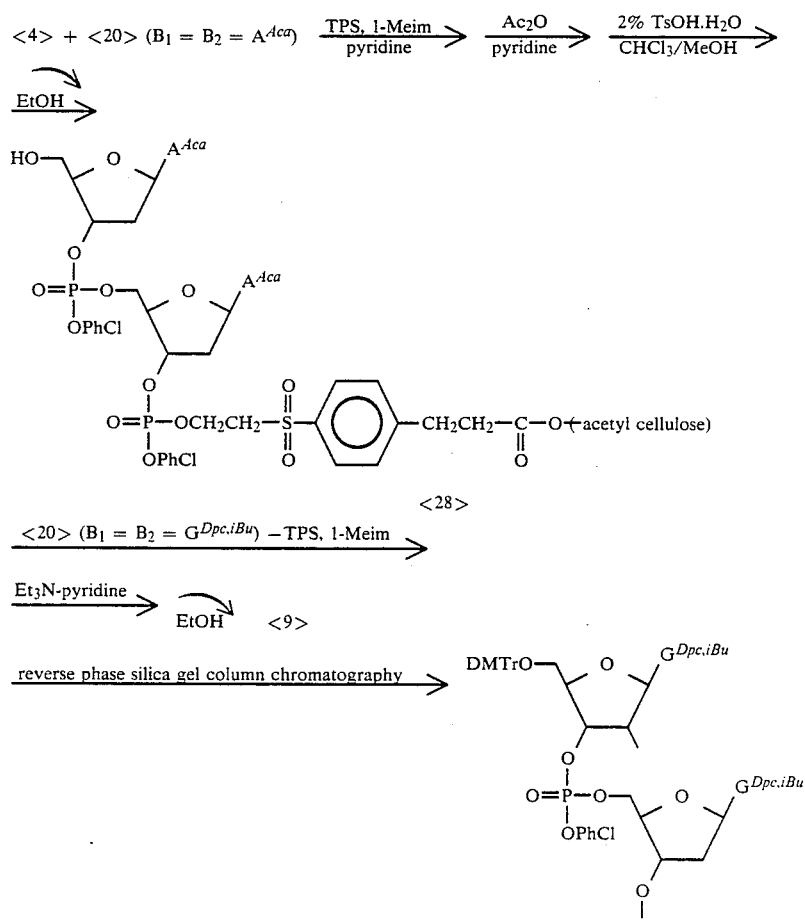

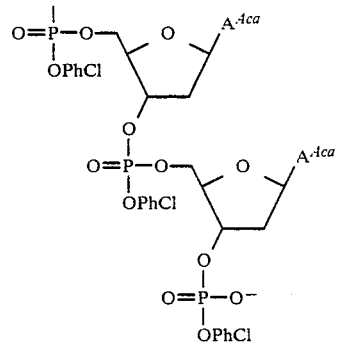

<27>

The acetyl cellulose derivative <4> (1.63 mmol/g) (0.3750 g, 0.604 mmol) obtained in Example 1 and <20> (B₁=B₂=A^{Aca}) (0.6140 g, 0.405 mmol) obtained in Example 11 were subjected to azeotropic dehydration with pyridine (5 ml×3 times) to remove water in the mixture) and the mixture was dissolved in pyridine (10 ml). Then, 2,4,6-triisopropylbenzenesulfonyl chloride (0.3660 g, 1.21 mmol) and 1-methylimidazole (0.20 ml, 2.48 mmol) were added to the solution and the mixture was stirred at room temperature for 4 hours. Cold water (0.5 ml) was added to the reaction solution to stop the reaction, the reaction solution was concentrated under a reduced pressure, and the residue was subjected to azeotropic dehydration with pyridine (5 ml×3 times) to remove water in the mixture. The residue was dissolved in pyridine (7.5 ml) and acetic anhydride (2.5 ml) was added to the solution, and the mixture was stirred at room temperature for 5 hours. The reaction solution was concentrated under a reduced pressure, and a small amount of toluene was added to the concentrate and distillation under a reduced pressure was repeated until the pyridine smell disappeared (0.345 mmol/g, condensation yield=94%).

The residue was dissolved in a solution (20 ml) of p-toluenesulfonic acid monohydrate (0.5412 g) in chloroform - methanol (7:3 v/v), and the solution was stirred at 0° C. for 15 minutes, neutralized with pyridine and concentrated under reduced pressure. The residue was dissolved in methylene chloride (10 ml) and the solution was dropped into ethanol (100 ml) with violent stirring. The formed precipitate was recovered by filtration and dried under a reduced pressure to obtain powdery <28> (B₁=B₂= in a yield of 76% (0.7720 g, 0.306 mmol; 0.397 mmol/g).

Then, <28> (B₁=B₂=A^{Aca}) and <20> (B₁=B₂=G^{Dpc,iBu}) (0.6710 g, 0.36 mmol) obtained in Example 12 were subjected to azeotropic dehydration with pyridine (5 ml×3 times) to remove water in the mixture, and the mixture was dissolved in pyridine (10 ml) and 2,4,6-triisopropylbenzenesulfonyl chloride (0.3336 g, 1.1 mmol) and 1-methylimidazole (0.18 ml, 2.21 mmol) were added to the solution. The mixture was stirred at room temperature for 4 hours, and cold water (0.5 ml) was added to the reaction solution. The mixture was stirred at room temperature for 30 minutes and concentrated under a reduced pressure.

The residue was dissolved in triethylamine pyridine (1:3 v/v) (20 ml), the solution was stirred at room temperature for 2 hours, and concentrated under a reduced pressure. The residue was dissolved in methylene chloride (10 ml) and the solution was dropped into ethanol (100 ml) with violent stirring to precipitate the acetyl cellulose derivative residue <9> converted to a sulfonylalkene, which was removed by filtration. The filtrate was concentrated under reduced pressure and separated by the reverse phase silica gel column chromatography (10 to 40% acetone - 0.05 M TEAB system) to obtain <27> (B₁=B₂=A^{Aca}, B₃=B₄=G^{Dpc,iBu}) in a yield of 69% (0.6000 g, 0.21 mmol).

The physical property value of <27>(B₁=B₂=A^{Aca}, B₃=B₄=G^{Dpc,iBu}) is as follows.

Rf value: 0.17 (acetone - water, 7:3 v/v)

EXAMPLE 15

Synthesis of octa-2'-deoxvribonucleotide <29> (GoGoAoAoTpToCoC) bv using acetyl cellulose derivative <4>

According to the following reaction formula, an acetyl cellulose derivative <30> having 2'-deoxycytidine 3'-succinate supported thereon was synthesized from the acetyl cellulose <4>, an acetyl cellulose derivative <31> having octa-2'-deoxyribonucleotide supported thereon is synthesized from <30>, and the protecting groups were removed from <31> and purification was carried out to obtain octa-2'-deoxyribonucleotide <29> (GpGpApApTpTpCpC):

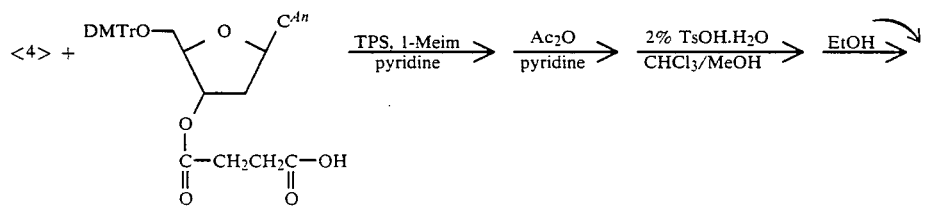

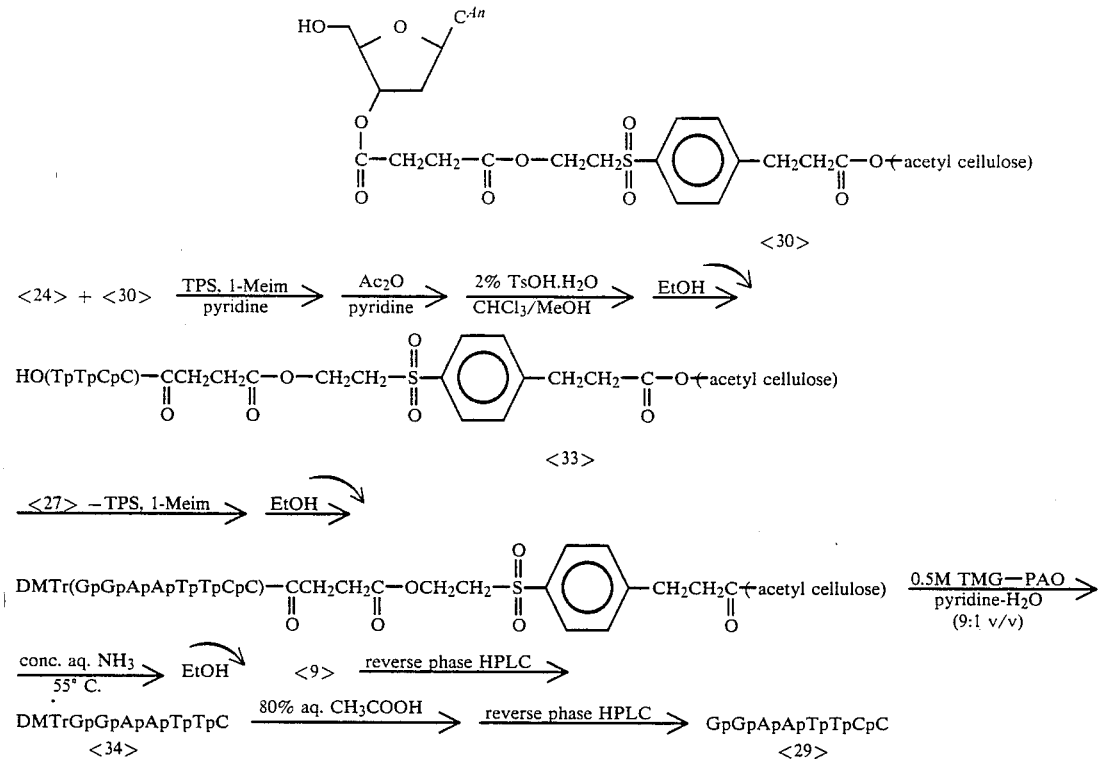

(i) Synthesis of acetyl cellulose derivative <30> having 2'-deoxycytidine 3'-succinate supported thereon The acetyl cellulose derivative <4> (1.63 mmol/g) (0.9663 g, 1.58 mmol) and N⁴anisoyl-3'-O-(3-carboxy)-propionyl-5,'O-dimethoxytrityl-2'-deoxycytidine <32> (0.802 g, 1.05 mmol) were subjected to azeotropic dehydration with pyridine (5 ml ×3 times), and the mixture was dissolved in pyridine (10.5 ml), and 2,4,6-triisopropylbenzene-sulfonyl chloride (0.9450 g, 3.15 mmol) and 1-methylimidazole 53 ml, 6.3 mmol) were added to the solution and the mixture was stirred at room temperature for 2 hours. Cold water (1 ml) was added to the reaction solution and the mixture was stirred for 30 minutes, methylene chloride (100 ml) was added, and the mixture was washed with water (40 ml). The organic layer was concentrated under a reduced pressure and the concentrate was subjected to azeotropic dehydration with pyridine (5 ml ×3 times). Acetic anhydride - pyridine (1:3 v/v) (20 ml) was added to the residue and the mixture was stirred at room temperature for 5 hours. The reaction solution was concentrated under a reduced pressure, and a small amount of toluene was added to the residue and azeotropic distillation was conducted until the pyridine smell disappeared (0.5 mmol/g, condensation yield=98%). The residue was dissolved in chloroform methanol (7:3 v/v) (10 ml) and the solution was cooled to 0° C., and a solution (10 ml) of p-toluenesulfonic acid monohydrate (0.5412 g) in chroloform - methanol (7:3 v/v) was added to the above solution. The mixture was stirred for 15 minutes and neutralized with pyridine, and the reaction solution was concentrated under a reduced pressure. The residue was dissolved in methylene chloride (20 ml) and the solution was dropped into ethanol (200 ml) with violent stirring. The formed precipitate was recovered by filtration and dried under a reduced pressure to obtain powdery <30> in a yield of 84% (1.3190 g, 0.877 mmol; 0.665 mmol/g).

(ii) Synthesis of acetyl cellulose derivative <31> having octa-2'-deoxvribonucleotide supported thereon <24> ($B_1=C^{An}$, $B_2=B_3=T^{BZ}$) (0.2735 g, 0.132 mmol) obtained in Example 13 and <30> (0.4910 g, 0.33 mmol) obtained in i) above were subjected to azeotropic dehydration with pyridine (5 ml ×3 times) to remove water from the mixture, and the mixture was dissolved in pyridine (3.3 ml) and 2,4,6-triisopropylbenzenesulfonyl chloride (0.1599 g, 0.528 mmol) and 1-methylimidazole (0.09 ml, 1.06 mmol) were added to the solution. The mixture was stirred at room temperature for 2 hours and cold water (0.5 ml) was added to the reaction solution, and the mixture was stirred at room temperature for 30 minutes and concentrated under a reduced pressure. The residue was subjected to azeotropic dehydration with pyridine (5 ml ×3 times) to remove water from the mixture. The residue was dissolved in pyridine (15 ml) and acetic anhydride (5 ml) was added to the solution, and the mixture was stirred at room temperature for 5 hours. The reaction solution was concentrated under a reduced pressure, and a small amount of toluene was added to the concentrate and distillation under a reduced pressure was conducted until the pyridine smell disappeared (0.163 mmol/g, condensation yield=93%). Then, the residue was dissolved in chloroform - methanol (10 ml) and the solution was cooled to 0° C., and a solution (10 ml) of p-toluenesulfonic acid monohydrate (0.5412 g) in chloroform - methanol (7:3 v/v) was added to the above solution. The mixture was stirred for 15 minutes and neutralized with pyridine, and the reaction solution was concentrated under a reduced pressure. The residue was dissolved in methylene chloride (10 ml) and the solution was dropped into ethanol with violent stirring. The formed precipitate was recovered by filtration and dried under a reduced pressure to obtain powdery <33> in a yield of 86% (0.6685 g, 0.115 mmol; 0.171 mmol/g).

<33> (0.445 g, 0.076 mmol) and <27> (B$_5$=B$_6$=B$_7$=B$_8$=G$^{Dpc,iBu}$) (0.4343 g, 0.152 mmol) obtained in Example 14 were subjected to azeotropic dehydration with pyridine (5 ml×3 times), and the mixture was dissolved in pyridine (3.4 ml) and 2,4,6-triisopropylbenzenesulfonyl chloride (0.1726 g, 0.57 mmol) and 1-methylimidazole (0.09 ml, 1.14 mmol) were added to the solution and the mixture was stirred at room temperature for 2 hours. Cold water (0.5 ml) was added to the reaction solution and the mixture was stirred at room temperature for 30 minutes and concentrated under a reduced pressure (condensation yield=80.43%). The residue was dissolved in methylene chloride (10 ml) and the solution was dropped into ethanol (100 ml) with violent stirring. The formed precipitate was recovered by filtration and dried under a reduced pressure to obtain powdery <31> in a yield of 91% (0.6120 g, 0.069 mmol; 0.113 mmol/g).

(iii) Removal of orotectino orouos from octamer <31> and purification

Figure 4:
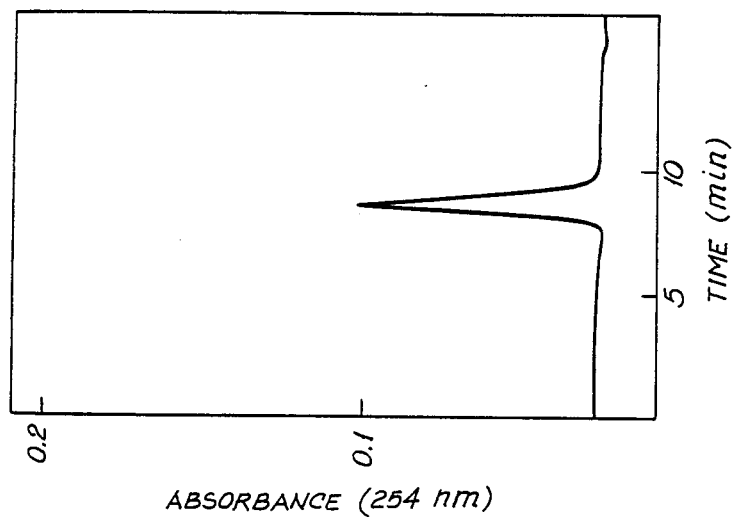
Figure 3:
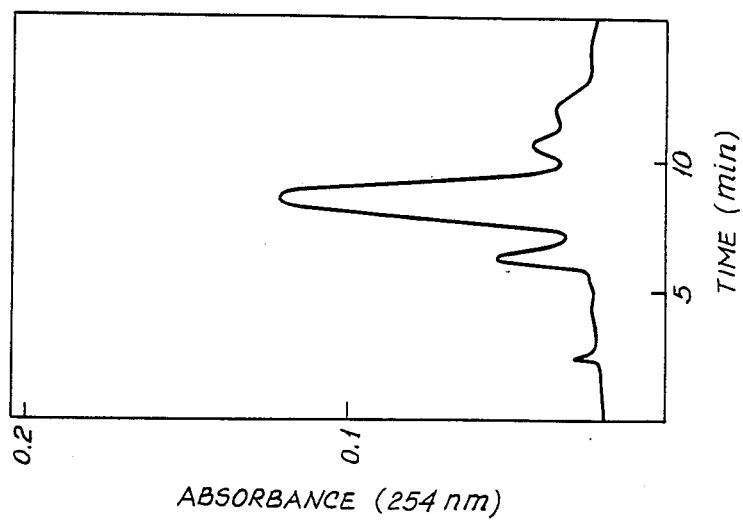
FIG. 3 is a chromatogram obtained a reverse phase high-performance liquid chromatography of an oligonucleotide (DNA type octamer) from which the protecting groups have been completely removed, obtained in an example (Example 15) of the present invention; and, FIG. 4 is a chromatogram obtained by again subjecting a purified product of the oligonucleotide shown in FIG. 3 to chromatography.

The octamer <31> (30 mg, 3.39 mmol) obtained in (ii) above was dissolved in a 0.5 M solution of N$^1$,N$^1$,N$^3$N$^3$-tetramethylguanidium (E)-2-pyridinealdoximate in pyridine - water (9:1 v/v) (0.6 ml), and the solution was allowed to stand at room temperature for one day. Ethanol (30 ml) was added to the reaction solution to precipitate the residual portion (9) of the acetyl cellulose derivative, which was removed by filtration. The filtrate was concentrated under a reduced pressure. Concentrated aqueous ammonia (28%) (20 ml) was added to the residue, and the mixture was sealed and allowed to stand at 55° C. for 6 hours, followed by concentration under a reduced pressure. The octamer residue dissolved in a 50 mM aqueous solution of TEAB (20 ml) was injected into SEP-PAK (C-18) supplied by Waters Co.), which had been allowed to stand for more than 3 hours after injection of acetonitrile - water (9:1 v/v) (10 ml) and then washed with a 50 mM aqueous solution of TEAB (20 ml). Then, N$^1$,N$^1$,N$^3$,N$^3$-tetramethylguanidine (E)-2-pyridinealdoximate was eluted with 5% acetonitrile - 0.05 mM TEAB aqueous solution (20 ml) and the octamer was then eluted with 10% acetonitrile - 0.05 M TEAB aqueous solution (20 ml) or 15% acetonitrile - 0.05 M TEAB aqueous solution (10 ml). The eluate was concentrated under a reduced pressure, and the residue was dissolved in water (1 ml), and the sample (0.63 ml) was collected and the octamer <34> having a dimethoxytrityl group at the 5'-position was purified by HPLC. The central fraction of the main peak was collected and concentrated under a reduced pressure. Water (1 ml) was added to the residue and distillation under a reduced pressure was conducted until the triethylamine smell disappeared. Then, an 80% aqueous solution of acetic acid (1.31 ml) was added to ½ of the collected sample, and the mixture was stirred at room temperature for 30 minutes. The reaction solution was concentrated under a reduced pressure, and a small amount of water was added to the residue and acetic acid was removed by azeotropic distillation. The residue was dissolved in water (1 ml), and the sample (0.46 ml) was purified by HPLC (LiChrosorb RP-18, 4 mm in inner diameter×250 mm in length, 10% acetonitrile - 0.1 M TEAA aqueous solution) (the obtained results are shown in FIG. 3). The central fraction of the main peak was collected and the eluate was concentrated under a reduced pressure to 1.95 OD of the octamer <29> from which all of the protecting groups had been removed (the results are shown in FIG. 4).

(iv) Confirmation of structure of octamer <29> (GpGpApApTpTpCpC)

The octamer <29> (0.6 OD) was dissolved in 0.05 M tris-buffer (pH 8.48) (200 μl), phosphodiesterase (20 μg) was added to the solution and the mixture was allowed to stand at 37° C. for 2 hours. Then, alkaline phosphatase (50 μg) was added to the mixture, and the mixture was allowed to stand at 25° C. for 1 hour. The enzyme decomposition product was separated by HPLC [Lichrosorb RP-18, 4 mm in inner diameter×250 mm in length, 10% acetonitrile - 0.1 M sodium phosphate aqueous solution (pH 4.2)], and it was confirmed that <29> was completely decomposed to the respective 2'-deoxynucleotides.

INDUSTRIAL APPLICABILITY

With the rapid progress of biochemistry or genetric engineering, especially with the development of the recombination DNA technique, the demand for synthetic oligonucleotides has increased, and the present invention is valuable for meeting this demand.

Synthetic DNA is used for the synthesis of structural genes such as human interferons and human growth hormones, and furthermore, use of synthetic DNA decamers through eicosamers for the production of primers for a determination of sequences, linkers for cloning, probes for a selection and confirmation of intended genes, agents for a direct diagnosis (genetic diagnosis) of microorganism-infectious diseases, and medicines such an anti-virus agents in the medicinal and therapeutic fields and the like has been remarkably increased. Primers, linkers and probes have specific sequences and large quantities of high-purity DNA oligomers are necessary for their production. The process of the present invention, which is simple and suitable for this large-quantity synthesis, makes a great contribution to their production.

RNA is located at a position intermediate between DNA and a protein in the protein biosynthesis system and has an important role. However, there are many unknown points, and in order to clarify the functions, it is desired to obtain RNA having an optional sequence in large quantities. According to the process using an enzyme, RNA is obtained only in a small amount and the intended sequence is restricted. Accordingly, the chemical synthesis process is very advantageous. But, according to the conventional liquid phase phosphotriester process, it is very difficult to obtain high-purity RNA oligomers such as decamers in large quantities. Furthermore, in the solid phase phosphotriester process, a general method of the synthesis of RNA oligomers, as established in the synthesis of DNA oligomers, has not been established.

The process of the present invention is very valuable as the process for preparing easily and in large quantities DNA oligomers and RNA oligomers, the synthesis of which is extremely laborious and cumbersome.

We claim:

1. A compound for forming a polysaccharide derivative protecting group, which is represented by the following general formula (I):

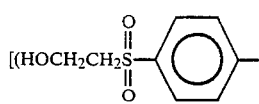
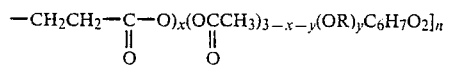 (I)
wherein $C_6H_7O_2$ stands for an anhydrous glucose residue, R stands for
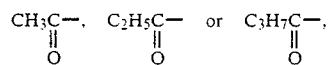
n is a number of 10 to 2,000, x is a number of 0.4 to 0.8, and y is a number of 1.0 to 2.0.
2. A compound as set forth in claim 1, wherein R in the formula (I) is
* * * * *